(12) United States Patent
Abe et al.

(10) Patent No.: US 7,872,745 B2
(45) Date of Patent: Jan. 18, 2011

(54) PATTERN INSPECTION APPARATUS AND PATTERN INSPECTION METHOD

(75) Inventors: Takayuki Abe, Kanagawa (JP); Tomohiro Iijima, Shizuoka (JP); Hideo Tsuchiya, Tokyo (JP); Tetsuyuki Arai, Kanagawa (JP)

(73) Assignee: NuFlare Technology, Inc., Numazu-shi (JP)

( * ) Notice: Subject to any disclaimer, the term of this patent is extended or adjusted under 35 U.S.C. 154(b) by 302 days.

(21) Appl. No.: 12/186,874

(22) Filed: Aug. 6, 2008

(65) Prior Publication Data
US 2009/0040513 A1    Feb. 12, 2009

(30) Foreign Application Priority Data

Aug. 8, 2007    (JP)    ............... 2007-206344
Aug. 24, 2007    (JP)    ............... 2007-218356
Jun. 17, 2008    (JP)    ............... 2008-157399

(51) Int. Cl.
*G01N 21/00*    (2006.01)

(52) U.S. Cl. .................. 356/237.5; 356/237.4

(58) Field of Classification Search .... 356/237.1–237.6
See application file for complete search history.

(56) References Cited

U.S. PATENT DOCUMENTS 6,909,501 B2    6/2005    Ogawa et al.
7,525,659 B2 *    4/2009    Furman et al. ............... 356/400
2004/0146295 A1    7/2004    Furman et al.

FOREIGN PATENT DOCUMENTS

JP    2002-107912    4/2002
JP    2007-102153    4/2007

* cited by examiner

*Primary Examiner*—Gregory J Toatley
*Assistant Examiner*—Tri T Ton
(74) *Attorney, Agent, or Firm*—Oblon, Spivak, McClelland, Maier & Neustadt, L.L.P.

(57) ABSTRACT

A pattern inspection apparatus includes a light source configured to emit a pulsed light, a stage on which an inspection target workpiece is placed, a sensor, including a plurality of light receiving elements two-dimensionally arrayed, configured to capture a pattern image in a two-dimensional region of the inspection target workpiece which is irradiated with the pulsed light, by using the plurality of light receiving elements, and a comparing unit configured to compare data of the pattern image with predetermined reference pattern image data, wherein the stage moves to be shifted by a number of pixels, being the number of natural number times one pixel, between pulses of the pulsed light.

8 Claims, 16 Drawing Sheets

(X,Y)  
Observed Position (X',Y')  
Original Position

PATTERN INSPECTION APPARATUS AND PATTERN INSPECTION METHOD

CROSS-REFERENCE TO RELATED APPLICATION

This application is based upon and claims the benefit of priority from the prior Japanese Patent Application No. 2007-206344 filed on Aug. 8, 2007 in Japan, and the prior Japanese Patent Application No.2007-218356 filed on Aug. 24, 2007 in Japan, and the prior Japanese Patent Application No. 2008-157399 filed on Jun. 17, 2008 in Japan, the entire contents of which are incorporated herein by reference.

BACKGROUND OF THE INVENTION

1. Field of the Invention

The present invention relates to a pattern inspection apparatus and a pattern inspection method. For example, it relates to an inspection apparatus and method for inspecting a pattern using pulsed lights.

2. Description of Related Arts

In recent years, with an increase in high integration and large capacity of a large-scale integrated circuit (LSI), a circuit line width required for semiconductor elements is becoming narrower and narrower. These semiconductor elements are manufactured by exposing and transferring a pattern onto a wafer to form a circuit by means of a reduced projection exposure apparatus (a so-called stepper) while using a master or "original" pattern (also called a mask or a reticle, and hereinafter generically called a mask) on which a circuit pattern is written, "drawn" or "formed". Therefore, in order to manufacture a mask for transfer printing a fine circuit pattern onto a wafer, an electron beam pattern writing apparatus capable of writing a fine circuit pattern needs to be employed. The pattern circuit may be directly written onto a wafer by the pattern writing apparatus. In addition to the writing apparatus using electron beams, a laser beam writing apparatus which uses laser beams to write a pattern is also under development.

Since a lot of manufacturing cost is needed for the production of LSI, an improvement in yield is a crucial issue. However, as typified by a DRAM (Dynamic Random Access Memory) of 1 giga-bit class, the order of a pattern constituting the LSI has been changing from submicron to nano-meter. Then, one of major factors that decrease the yield is a pattern defect of a mask used in exposing and transferring an ultrafine pattern onto a semiconductor wafer by a photolithography technique. In recent years, with miniaturization of an LSI pattern formed on a semiconductor wafer, dimensions to be detected as a pattern defect have become extremely small. Therefore, a pattern inspection apparatus for inspecting defects of a transfer mask used in manufacturing the LSI needs to be highly accurate.

On the other hand, with development of multimedia technologies, the size of a liquid crystal substrate of an LCD (Liquid Crystal Display) is becoming large, e.g., 500 mm×600 mm or more, and a pattern of a TFT (Thin Film Transistor) or the like formed on the liquid crystal substrate is becoming minute. Therefore, it is increasingly required to inspect an ultra-fine pattern defect in a large area. For this reason, development of a pattern inspection apparatus which, in a short time, efficiently inspects defects of a pattern of a large-area LCD and a photomask used in manufacturing the large-area LCD is urgently required.

As to a conventional pattern inspection apparatus, it is well-known that inspecting is performed by comparing an optical image captured by photographing a pattern formed on a target workpiece or "sample", such as a lithography mask, at a predetermined magnification by use of a magnification optical system with design data or an optical image captured by photographing the same pattern in a different region on the target workpiece. For example, the following is known as pattern inspection methods: "die to die inspection" that compares optical image data obtained by capturing images of the same patterns at different positions on the same mask, and "die to data base inspection" that performs inputting writing data (design pattern data), which is generated by converting pattern CAD data into an appropriate format to be input by a writing apparatus when writing a pattern on a mask, into an inspection apparatus, generating design image data (reference image) based on the inputted writing data, and comparing the design image data with an optical image serving as measurement data obtained by capturing the image of the pattern. In the inspecting methods of the inspection apparatus, the target workpiece is placed on a stage to be scanned by a flux of light while the stage is moving to perform inspection. The target workpiece is irradiated with a flux of light from a light source and an irradiation optical system. Light transmitted through the target workpiece or reflected by the target workpiece is focused on a sensor through the optical system. The image captured by the sensor is transmitted to a comparison circuit as measurement data. In the comparison circuit, after position alignment of the images, the measurement data and the reference data are compared based on an appropriate algorithm. When the measurement data is different from the reference data, it is judged that there is a pattern defect (refer to, e.g., Japanese Unexamined Patent Publication No. 2007-102153 (JP-A-2007-102153)).

Conventionally, continuous light is used as irradiation light. In order to detect finer defects, it is necessary to use a light of short wavelength in the pattern inspection apparatus. As the light of short wavelength, a KrF excimer laser with a wavelength of 248 nm or an ArF excimer laser with a wavelength of 193 nm can be exemplified. However, the excimer laser is a pulsed laser. Moreover, in recent years, although new type of laser apparatuses that consist of only solid state lasers and are capable of emitting a laser of 193 nm have been produced, they use pulsed lasers. That is, lights of short wavelengths are pulsed laser lights in many cases as stated above. Such pulsed lasers oscillate at a frequency of 1 kHz to several MHz. Moreover, emission of only about several (n) seconds per pulse can be obtained. Furthermore, a light intensity difference of about 30% is generated per pulse light, thereby a large error occurs in the measured light quantity.

Conventionally, as light for illuminating a target workpiece, continuous light has been used. That is, the target workpiece is always illuminated to be in a bright state. Then, in this state, an optical image is captured while the stage is continuously moving at a fixed speed, using a line sensor of one-dimensional array which receives an image in one dimensional direction at a time, as a sensor for measuring a quantity of light of a pixel, for example. A region inspected during once continuous movement of the stage is hereinafter called a frame. Alternatively, instead of the one-dimensional line sensor, there is a case of using a sensor (TDI sensor) in which one thousand light receiving elements are arrayed perpendicularly to the stage movement and about five light receiving elements are arrayed in the movement direction. Each light receiving element of the TDI sensor measures light quantity during a predetermined time period and sends the measurement result to an adjoining light receiving element in the movement direction of the stage. The adjoining light receiving element adds a light quantity measured by itself during a predetermined time to the received measurement result, and sends the addition result to a further adjoining light receiving element. After repeating this, the total of the measured light quantity is output from the light receiving elements in the last row. By virtue of this, information on one pixel on the target workpiece is measured as the sum of the light intensity measured by the five light receiving sensors. In these conventional methods, it takes about two hours, for example, to inspect one target workpiece. In any case, it is the premise that continuous light is used and the measurement region of the target workpiece is always illuminated to be in a bright state. Thereby, by utilizing this, the quantity of light from each region is measured to inspect defects.

However, if these methods are intact, they cannot be used for a pulsed laser. FIG. 18 shows an example of a photoperiod and a light quantity of a pulsed laser light source. In FIG. 18, pulsed lights 92, 94, and 96 emit lights at the period of T. In this case, as mentioned above, the period T is 1 kHz to several MHz, and the light emission time is about several (n) seconds, and then, only at the moment, light information from the target workpiece can be obtained. In addition, since the quantity of light changes no less than 30% per pulse, when the stage is continuously moved at the conventional stage speed, the measurement result of the light quantity has a large error, and then it is impossible to accurately inspect defects.

Now, the inspection region is assumed to be 10×10 cm. Regarding the number of light receiving elements, one is arrayed in the direction of the stage movement and two thousand are arrayed perpendicularly to the stage movement. One light receiving element is assumed to be able to measure a light quantity of the region of 100 nm×100 nm on the target workpiece. In this case, the frame width (at right angles to the direction of continuous movement of the stage) is 100 nm×2000 pieces=200 μm=0.2 mm. The number of frames is 10 cm/0.2 mm=500. It is herein assumed that the inspection time is suppressed to be two hours or twenty hours, for example, and in that case, the inspection time per frame of the stage is 14.4 seconds or 144 seconds. Since the frame length (direction of continuous movement of the stage) is 10 cm, the stage speed at this time is 10 cm/14.4 seconds=6.94 mm/second, or 10 cm/144 seconds=0.694 mm/second. On the other hand, when the oscillation frequency of the pulsed laser is assumed to be 40 kHz, the oscillation period is 1/40 kHz=0.025 msecond=25 μsecond. When a pulsed laser illuminates the target workpiece, the sensor measures the quantity of light of a certain position, and a next pulsed laser illuminates the target workpiece in 25 micro seconds, since the stage and the target workpiece are moving, their movement amount is 6.94 mm/second×25 micro seconds=173.5 nm or 0.694 mm/second×25 micro seconds=17.35 nm. The number of times of irradiation times of the pulsed laser used per pixel is 100 nm/173.5 nm=0.57 times in the former case, and 5.7 times in the latter case. As mentioned above, since the light quantity of each pulse changes about 30%, changes of the measured light quantity per pixel are $30\%/\sqrt{0.57}=39.73\%$ and $30\%/\sqrt{5.7}=12.6\%$ respectively, and they serve as measurement errors of the light quantity, which makes it difficult to pass the inspection.

Although the above example is the case of using a line sensor, another case of using the TDI sensor mentioned above is almost the same as the line sensor case as follows: When five light receiving elements are arrayed in a line in the direction of continuous movement of the stage, the number of irradiation times of a pulsed laser per pixel becomes five times. In this case, change of the measured light quantity per pixel becomes $30\%/\sqrt{(0.57\times5)}=17.77\%$ and $30\%/\sqrt{(5.7\times5)}=5.62\%$, which also makes it difficult to pass the inspection.

Furthermore, in the above-mentioned example of suppressing the mask inspection time to be two hours, the stage moves 173.5 nm during pulses, that is a time period after a certain pulse illuminates until a following pulse illuminates. Since the size of a pixel is 100 nm, this stage movement corresponds to a movement for 1.735 pixels, which is greater than 1 pixel by 0.735 pixel. This means that the (relative) position of the sensor proceeds further than the pixel existing next to another pixel which illuminated previously, by 0.735 pixel. Consequently, in the case of using the line sensor, the light quantity of 0.735 pixel (73.5%) in the pixel existing next to another pixel previously illuminated cannot be measured by the line sensor. Naturally, it is impossible to judge the existence of defects in this region that cannot be measured, which is a fatal problem in inspecting defects. Furthermore, in the case of using the TDI sensor, the following problems arise. When the sensor moves by 1.735 pixels, the position of one light receiving element of the TDI sensor extends over the boundary between two pixels. Therefore, one light receiving element measures a light quantity composed of two light quantities, that is a light quantity of 0.27 pixel and a light quantity of 0.73 pixel. Since this distribution ratio changes depending upon a pulse generating timing, the conventional method cannot control it. Consequently, information on a light quantity measured by the TDI sensor is composed of light quantity information on two pixels, which is mixed without controlling, thereby deteriorating the measurement precision and reducing the capability of inspecting defects.

Thus, when the conventional method of using continuous light is applied to the case of pulsed lasers, there exists a critical defect of being unable to accurately judge defects.

BRIEF SUMMARY OF THE INVENTION

In accordance with one aspect of the present invention, a pattern inspection apparatus includes a light source configured to emit a pulsed light, a stage on which an inspection target workpiece is placed, a sensor, including a plurality of light receiving elements two-dimensionally arrayed, configured to capture a pattern image in a two-dimensional region of the inspection target workpiece which is irradiated with the pulsed light, by using the plurality of light receiving elements, and a comparing unit configured to compare data of the pattern image with predetermined reference pattern image data, wherein the stage moves to be shifted by a number of pixels, being the number of natural number times one pixel, between pulses of the pulsed light.

In accordance with another aspect of the present invention, a pattern inspection apparatus includes a light source configured to emit a pulsed light, a stage on which an inspection target workpiece is placed, a sensor, including a plurality of light receiving elements two-dimensionally arrayed, configured to capture a pattern image in a two-dimensional region of the inspection target workpiece which is irradiated with the pulsed light, by using the plurality of light receiving elements, a comparing unit configured to compare data of the pattern image with predetermined reference pattern image data, and an opening-and-closing unit, arranged between the light source and the sensor, configured to let a predetermined number of pulses of the pulsed light pass to a side of the sensor by being opened and closed.

Furthermore, in accordance with one aspect of the present invention, a pattern inspection method includes emitting a pulsed light, capturing a pattern image in a two-dimensional region of an inspection target workpiece which is irradiated with the pulsed light, by using a sensor including a plurality of light receiving elements two-dimensionally arrayed, while moving a stage, on which the inspection target workpiece is placed, to be shifted by a number of pixels, being the number of natural number times one pixel, between pulses of the pulsed light, and comparing data of the pattern image with predetermined reference pattern image data, and outputting a comparing result.

Furthermore, in accordance with another aspect of the present invention, a pattern inspection method includes emitting a pulsed light of a predetermined number of pulses when an inspection target workpiece is stopped, capturing a pattern image in a two-dimensional region of the inspection target workpiece which is irradiated with the pulsed light, by using a sensor including a plurality of light receiving elements two-dimensionally arrayed, comparing data of the pattern image with predetermined reference pattern image data, and outputting a comparing result and moving the inspection target workpiece after the inspection target workpiece is irradiated with the pulsed light of the predetermined number of pulses.

DETAILED DESCRIPTION OF THE INVENTION

Each Embodiment below describes an inspection apparatus and method using a pulsed light source of short wavelength.

Embodiment 1

Figure 1:
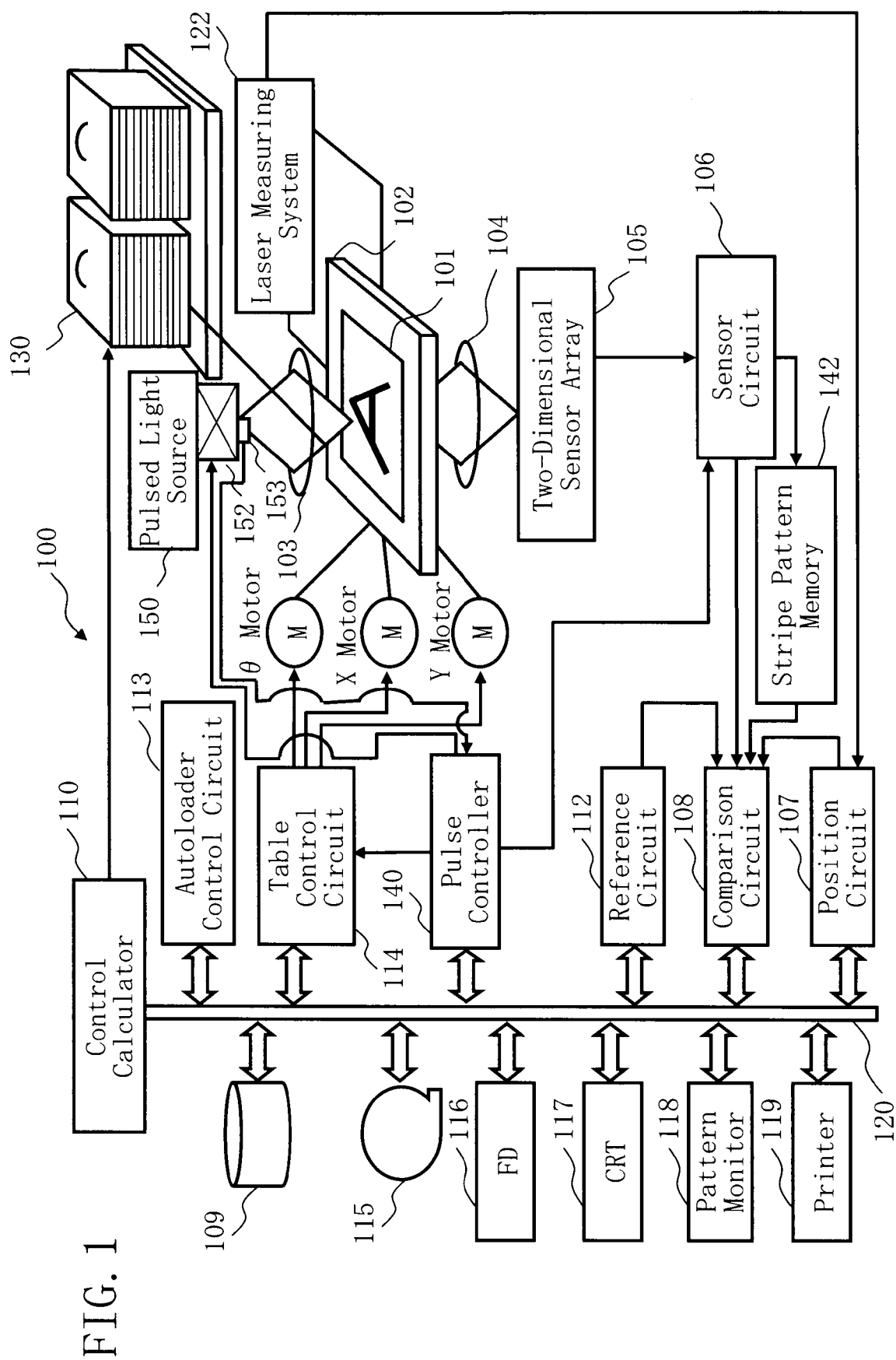
FIG. 1 shows a schematic diagram illustrating a structure of a pattern inspection apparatus described in Embodiment 1.

FIG. 1 shows a schematic diagram illustrating the structure of a pattern inspection apparatus described in Embodiment 1. In FIG. 1, an inspection apparatus 100 for inspecting defects of a target workpiece 100, for example a mask, includes an optical image acquisition unit and a control system circuit. The optical image acquisition unit includes a pulsed light source 150, a shutter 152, an optical sensor 153 using a photoelectric element, an XYθ table 102 (stage), an optical system 103, a magnifying optical system 104, a two-dimensional sensor array 105, a sensor circuit 106, a laser measuring system 122, and an autoloader 130. In the control system circuit, a control calculator 110 serving as a computer is connected, through a bus 120, to a position circuit 107, a comparison circuit 108, a reference circuit 112, an autoloader control circuit 113, a table control circuit 114, a magnetic disk drive 109, a magnetic tape drive 115, a flexible disk drive (FD) 116, a CRT 117, a pattern monitor 118, a printer 119, and a pulse controller 140. Moreover, the sensor circuit 106 is connected to a stripe pattern memory 142 which is connected to the comparison circuit 108. The XYθ table 102, which is an example of the stage, is driven by an X-axis motor, a Y-axis motor, and a θ-axis motor. FIG. 1 depicts structure elements necessary for describing Embodiment 1, and it should be understood that other structure elements generally necessary for the target workpiece inspection apparatus 100 may be included therein.

In the inspection apparatus 100, an inspection optical system of large magnification is composed of the pulsed light source 150, the shutter 152, the optical sensor 153 using a photoelectric element, the XYθ table 102, the optical system 103, the magnifying optical system 104, the two-dimensional sensor array 105, and the sensor circuit 106. The pulsed light source oscillates automatically at 40 kHz and generates a pulsed laser. When the shutter opens and a laser pulse passes through the shutter, the optical sensor 153, installed at the lower part of the shutter, detects the pulsed laser and sends a signal indicating that the pulse was generated, to the pulse controller 140. The XYθ table 102 is driven by the table control circuit 114 under the control of the control computer 110. The XYθ table 102 can be moved by a drive system such as a three-axis (X-Y-θ) motor, which drives the XYθ table 102 in the X direction, the Y direction, and the θ direction. A step motor, for example, can be used as these X, Y, and θ motors. The moving position of the XYθ table 102 is measured by the laser length measurement system 122 and supplied to the position circuit 107. A photomask 101 on the XYθ table 102 is automatically conveyed from the autoloader 130 driven by the autoloader control circuit 113, and automatically ejected after the inspection.

The photomask 101 serving as a target workpiece to be inspected, "inspection target workpiece", or "inspection sample" is placed on the XYθ table 102 which is movable in a horizontal direction and a rotating direction by the X-, Y-, and θ-axis motors. Then, the pattern written on the photomask 101 is illuminated with pulsed lights emitted by the pulsed light source 150, thorough the optical system 103. The illuminated pattern penetrates the photomask 101, the light is focused through the magnifying optical system 104 as an optical image on the two-dimensional sensor array 105, and the light receiving element measures the quantity of light of each pixel.

Figure 2:
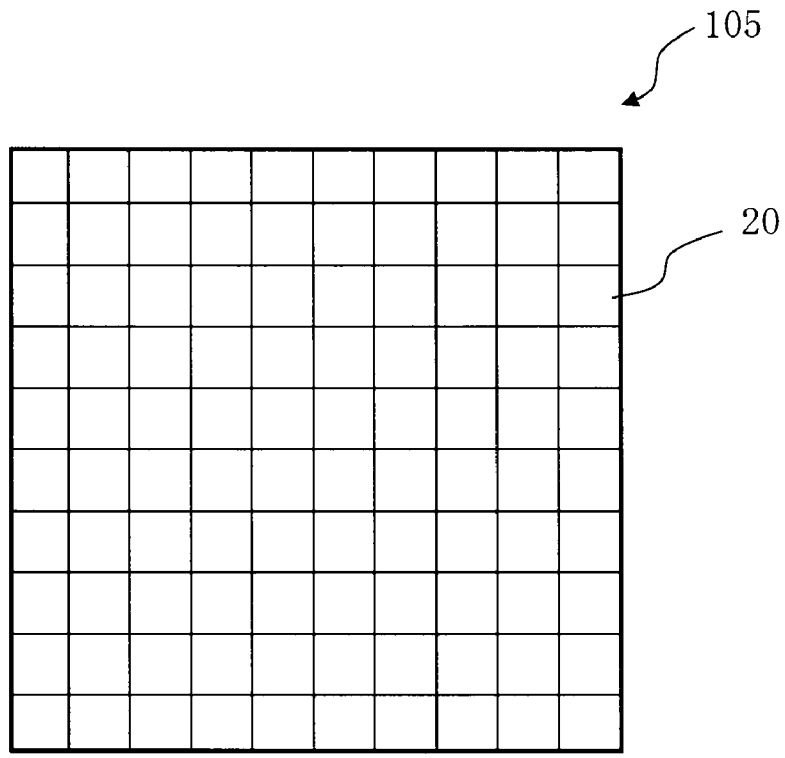
FIG. 2 shows an example of an arrangement state of a two-dimensional sensor array described in Embodiment 1.

FIG. 2 shows an example of an arrangement state of the two-dimensional sensor array described in Embodiment 1. In FIG. 2, the two-dimensional sensor array 105 includes a plurality of light receiving elements 20 which are two-dimensionally arrayed. Using these plural light receiving elements 20, a pattern image in the two-dimensional region of the photomask 101 which is irradiated by the pulsed lights is captured at a time. The capturing is performed as follows using the two-dimensional sensor array 105.

Figure 3:
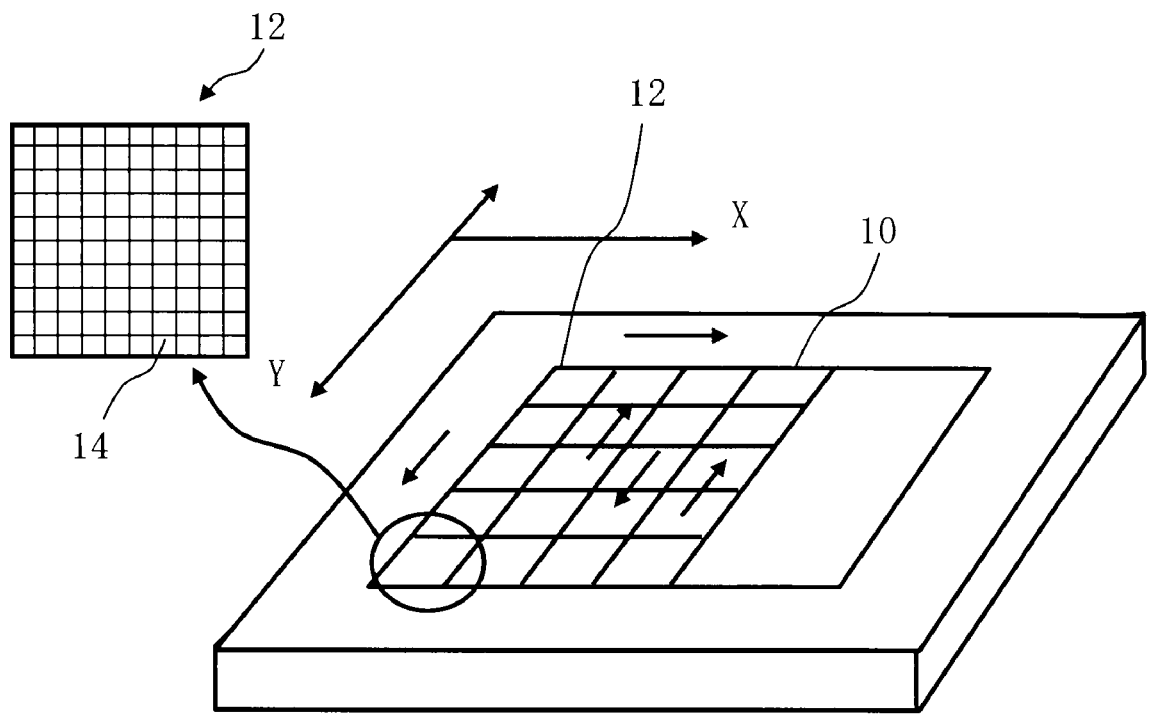
FIG. 3 shows a schematic diagram for illustrating a step of acquiring an optical image described in Embodiment 1.

FIG. 3 shows a schematic diagram for illustrating a step of acquiring an optical image in Embodiment 1. As shown in FIG. 3, the region to be inspected is virtually divided into a plurality of strip-like inspection stripes 10, each having a length in the Y direction and a width W in the X direction. While repeating moving and stopping in the Y direction, the movement of the XYθ table 102 is controlled so that each of the divided inspection stripes 10 can be scanned by a step and repeat method. Then, an optical image is acquired at the time of stopping. After acquiring the image in the first inspection stripe, similarly, an image of the width W in the second inspection stripe is input while the XYθ table 102 is moving reversely to the above direction by the step and repeat method. In the case of acquiring an image in the third inspection stripe, the image is acquired while the XYθ table 102 is moving reversely to the direction for acquiring the image in the second inspection stripe, i.e., moving in the same direction as that for acquiring the image in the first inspection stripe, by the step and repeat method. Thus, acquiring images in this manner makes it possible to reduce wasteful processing time. A two-dimensional image capture region 12, used for once capturing an image, includes a plurality of pixels 14 in the two-dimensional direction.

Figure 4:
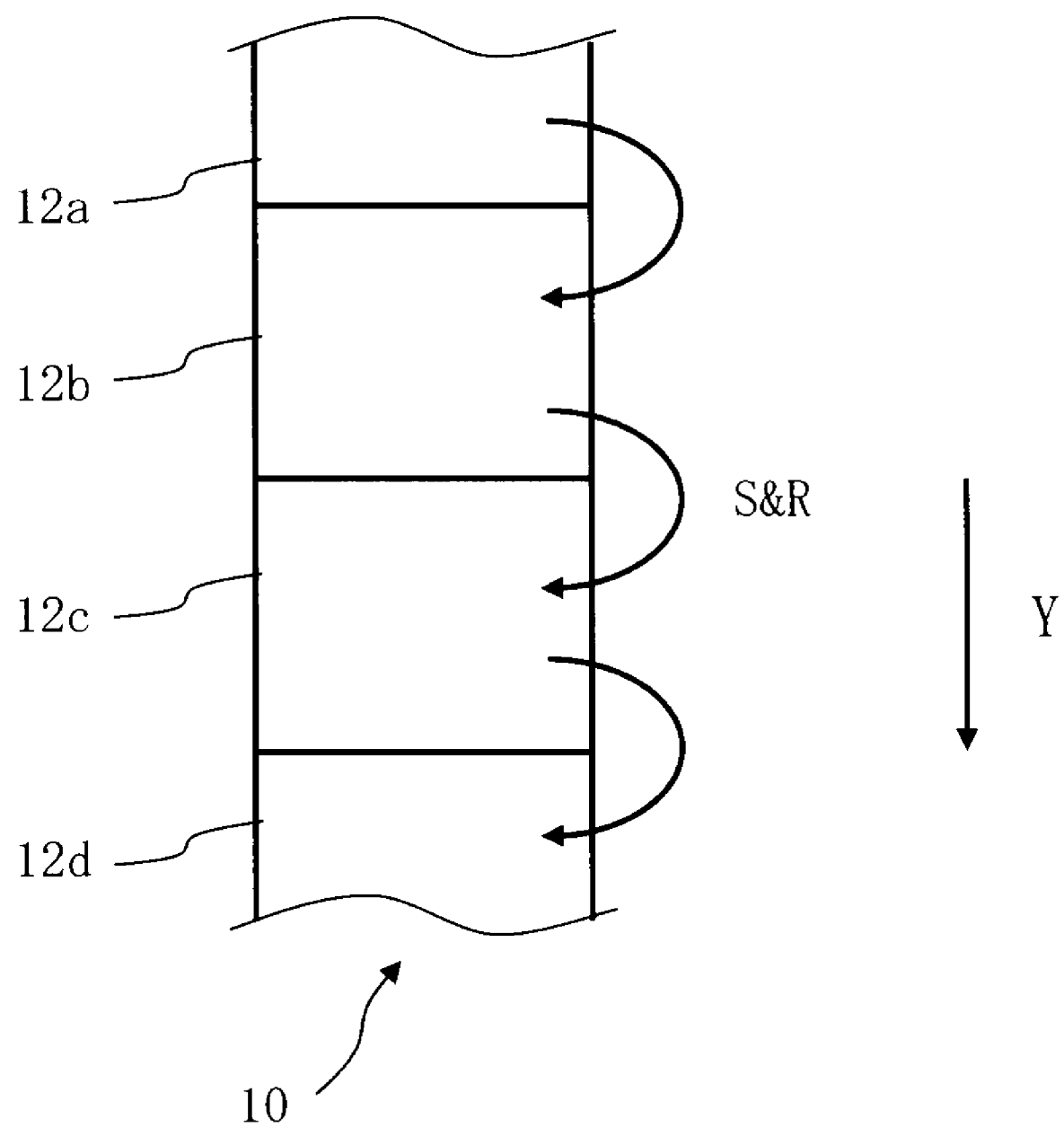
FIG. 4 shows another schematic diagram for illustrating a step of acquiring an optical image described in Embodiment 1.

FIG. 4 shows another schematic diagram for illustrating a step of acquiring an optical image in Embodiment 1. FIG. 4 shows the case where the X-direction width W of the inspection stripe 10 is set to be equivalent to the array width of the light receiving element in the X direction of the two-dimensional sensor array 105. For example, in the case of using the two-dimensional sensor array 105 where the light receiving elements 20 (e.g. photo-diodes) for 2000×2000 pixels are arranged, the two-dimensional image capture region 12 for capturing once is a region including 2000×2000 pixels. It is assumed in the following that the measurement position on the target workpiece is illuminated with pulsed lasers 1000 times when the state of the stage is stopped.

First, the XYθ table 102 is moved to the position where it is possible to capture a pattern image of a two-dimensional image capture region 12a of a certain inspection stripe 10 by the two-dimensional sensor array 105. As a light-emission step, the pulsed light source 150 continues emitting pulsed lights. The shutter 152 is arranged between the pulsed light source 150 and the two-dimensional sensor array 105. More specifically, the shutter 152 is arranged near the emission place of the pulsed light source 150. Opening and closing of the shutter 152 is controlled by the pulse controller 140. When the shutter is open, the optical sensor detects a pulsed laser and sends a signal to the pulse controller 140 at each detection. The pulse controller 140 counts the number of receiving times of the signals, and then, after checking the pulse having been generated 1000 times, closes the shutter. Thus, the shutter 152 lets a predetermined number of pulsed lights pass to the two-dimensional sensor array 105 side, by being opened and closed. Then, when the shutter 152 is opened, the target workpiece is illuminated with the predetermined number of pulsed lights. The shutter 152 serves as an example of an opening-and-closing unit. The illuminated portion of the target workpiece is focused on the two-dimensional sensor array 105. As an image capture step, when the state of the XYθ table 102 is stopped, the two-dimensional sensor array 105 captures a pattern image in the two-dimensional image capture region 12a of the photomask 101 which is irradiated with the pulsed lights. Therefore, in each light receiving element 20 of the two-dimensional sensor array 105, light quantity of the predetermined number of pulsed lights is to be accumulated. After the pulse controller checks that the two-dimensional sensor array 105 side is irradiated with the predetermined number of pulsed lights, the pulse controller closes the shutter 152. The image data acquired by the sensor is sent to the comparison circuit to be used for inspection. Similarly, the XYθ table 102 moves in the Y direction to the position of the next two-dimensional image capture region 12b. The movement of the XYθ table 102 is controlled by the table control circuit 114. The table control circuit 114 judges a timing for moving, based on a signal indicating the end of the emission and sent from the pulse controller 140. Then, after the moving (after checking that the image data has been transmitted to the comparison circuit), the shutter 152 opens when the state of the XYθ table 102 is stopped, and the predetermined number of pulsed lights are emitted. The two-dimensional sensor array 105 captures a pattern image in the two-dimensional image capture region 12b of the photomask 101 which is irradiated with the pulsed lights. When the two-dimensional sensor array 105 side is irradiated with the predetermined number of pulsed lights, the shutter 152 is closed. Then, the image data acquired by the sensor is sent to the comparison circuit to be used for inspection. Moreover, the XYθ table 102 further moves in the Y direction to the position of the following two-dimensional image capture region 12c. In this way, while the shutter 152 is open, the XYθ table 102 is stopped, and while the shutter 152 is closed, the XYθ table 102 moves to the position of the following two-dimensional image capture region 12 which is to be irradiated with the pulsed lights. As mentioned above, with repeating the step and repeat operation, capturing is performed up to the end of the inspection stripe 10 to acquire the optical image of the photomask 101.

Although there is illustrated in FIG. 4 the case where the X-direction width W of the inspection stripe 10 is set to be equivalent to the array width of the light receiving element in the X direction of the two-dimensional sensor array 105, it is not restricted thereto. For example, it is also suitable to set the X-direction width W of the inspection stripe 10 is set to be equivalent to N times the X-direction width of the two-dimensional sensor array 105.

Figure 5:
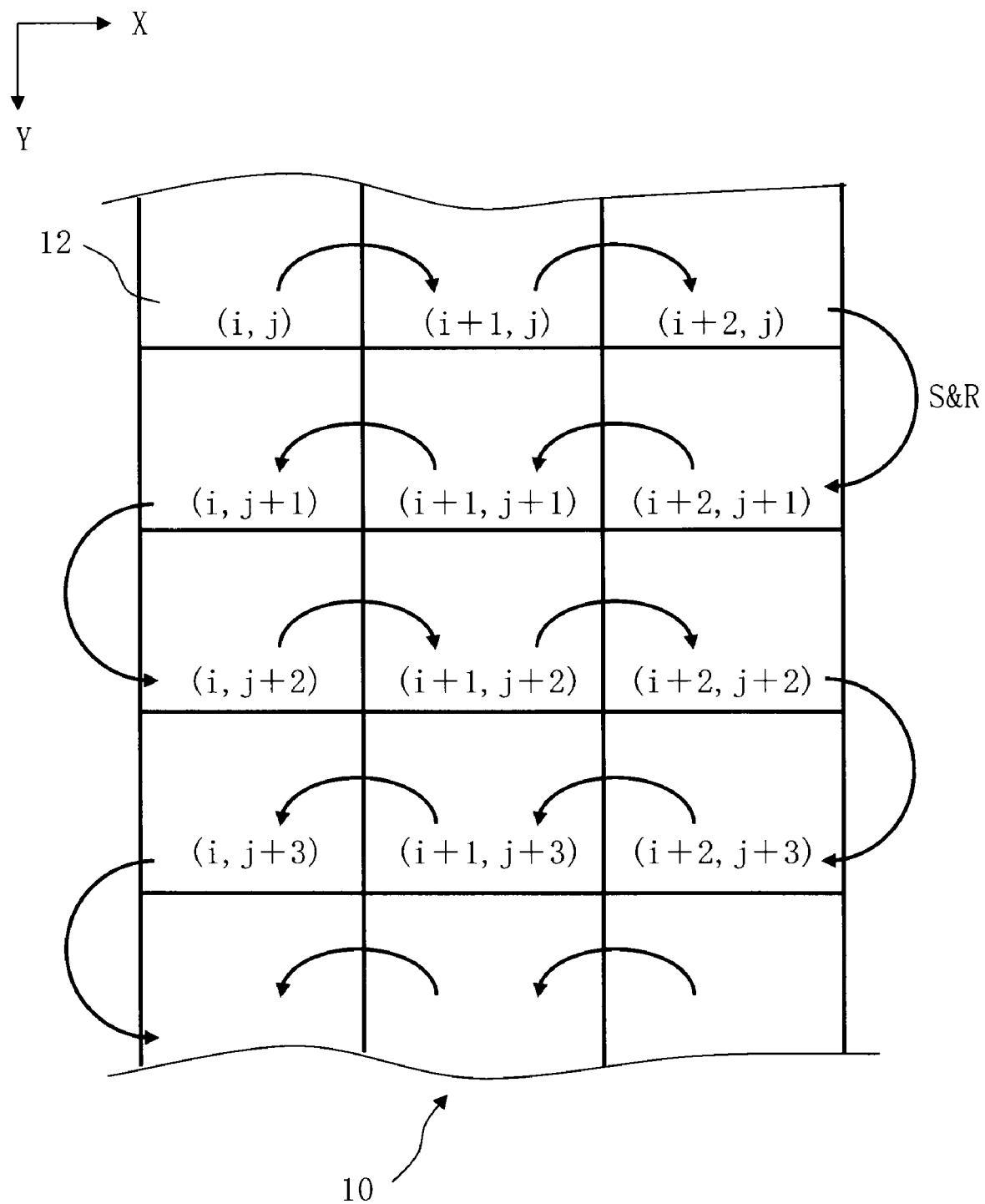
FIG. 5 shows another schematic diagram for illustrating a step of acquiring an optical image described in Embodiment 1.

FIG. 5 shows another schematic diagram for illustrating a step of acquiring an optical image in Embodiment 1. FIG. 5 shows the case where the X-direction width W of the inspection stripe 10 is set to be equivalent to three times the X-direction width of the two-dimensional sensor array 105. In the example of FIG. 4, the step and repeat operation is performed only in the Y direction. On the other hand, in FIG. 5, a pulsed light from the pulsed light source is further made to perform the step and repeat operation in the X direction.

Figure 6:
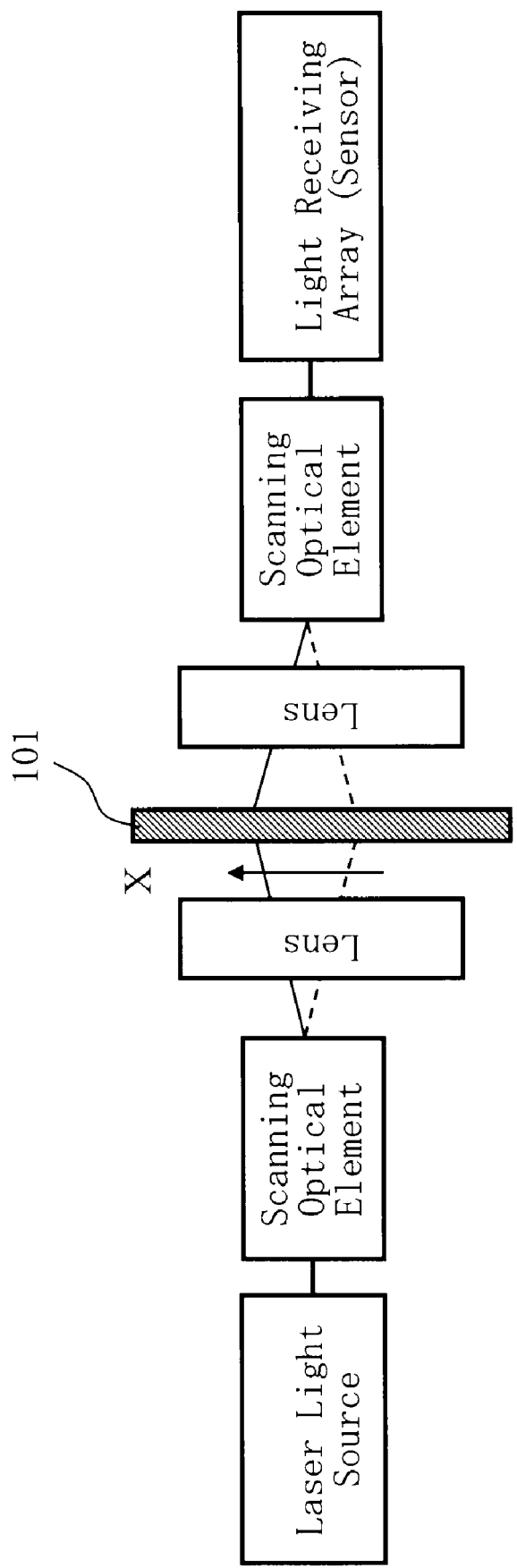
FIG. 6 shows a schematic diagram for illustrating the case of scanning a pulsed light described in Embodiment 1.

FIG. 6 shows a schematic diagram for illustrating the case of scanning the pulsed light in Embodiment 1. It is structured in FIG. 6 so that a scanning optical element, which uses an acoustooptic element, is arranged at the light source side, and an optical path of the pulsed laser light can be moved in the X direction on the target workpiece. Moreover, operating simultaneously with this, it is structured so that a pattern on the target workpiece can be focused on the sensor by changing the optical path of the laser by using a scanning optical element at the sensor side. By virtue of these two scanning optical elements, the two-dimensional image capture region 12 can be moved in the X direction by the step and repeat operation while the stage is stopped.

First, the XYθ table 102 is moved to the position where it is possible to capture a pattern image of the two-dimensional image capture region 12 indicated by coordinates (i, j) of a certain inspection stripe 10 by using the two-dimensional sensor array 105. The pulsed light source 150 continues emitting pulsed lights. As a light-emission step, the shutter 152 is open only while the predetermined number of pulses are emitted. Similarly to the example above mentioned, this is performed using information from the optical sensor, based on the control by the pulse controller. As an image capture step, while the state of the XYθ table 102 is stopped, the two-dimensional sensor array 105 captures a pattern image in the two-dimensional image capture region 12 of the coordinates (i, j). Therefore, light quantity of the predetermined number of pulses is accumulated in each light receiving element 20 of the two-dimensional sensor array 105. When the two-dimensional sensor array 105 side is irradiated with the predetermined number of pulsed lights, the shutter 152 is closed. Then, the image data acquired by the sensor is sent to the comparison circuit to be used for inspection. At the same time, the optical path of the laser light is changed in the X direction by using the two scanning optical elements in order that the position of the two-dimensional image capture region 12 of coordinates (i+1, j) is irradiated to be focused on the sensor. After checking that the image data has been transmitted to the comparison circuit, the shutter 152 is opened at the position, it is irradiated with the predetermined number of pulsed lights. The two-dimensional sensor array 105 captures a pattern image of the two-dimensional image capture region 12 of the coordinates (i+1, j). When the two-dimensional sensor array 105 side is irradiated with the predetermined number of the pulsed lights, the shutter 152 is closed. Then, the image data acquired by the sensor is sent to the comparison circuit to be used for inspection. Similarly, after a pattern image in the two-dimensional image capture region 12 of coordinates (i+2, j) has been captured, while the state of the shutter 152 is closed, the image data acquired by the sensor is sent to the comparison circuit to be used for inspection. Simultaneously, the XYθ table 102 is moved in the Y direction to the position of the two-dimensional image capture region 12 of coordinates (i+2, j+1). Then, similarly, when capturing an image in the −X direction is finished up to the pattern image in the two-dimensional image capture region 12 of coordinates (i, j+1) by the step and repeat operation by the pulsed light source 151, the XYθ table 102 is moved in the Y direction to the position of the two-dimensional image capture region 12 of coordinates (i, j+2) while the state of the shutter 152 is closed. In this way, with repeating the step and repeat operation in the directions X and Y, capturing an image is repeatedly performed up to the end of the inspection stripe 10 to acquire the optical image of the photomask 101.

An example of computation of inspection time will be described below. It is assumed that the inspection region (measurement region) of the photomask 101 is L×L (cm), and the pixel size is p×p (nm). Then, there is used the two-dimensional sensor array 105 in which X×Y light receiving elements 20 (for example, photo-diodes) are arranged. Moreover, it is assumed that the number of pulses received at one place is K. When a pulsed laser light of N (kHz), for example, is used as an irradiation light, an image capturing time t(s) can be calculated by the following equation (1).

$$t = K \cdot L^2 \cdot 10^{11}/(p^2 \cdot N \cdot X \cdot Y) \quad (1)$$

For example, it is assumed that the inspection region (measurement region) of the photomask 101 is 10 cm×10 cm, and the pixel size is 100 nm at the pitch p=100 nm. Then, there is used the two-dimensional sensor array 105 in which light receiving elements 20 (for example, photo-diodes) of (2000 pieces in the length direction)×(2000 pieces in the width direction) (that is, X=2000, Y=2000) are arranged. In that case, the sensor region by the two-dimensional sensor array 105 is 0.2 mm×0.2 mm. The number of pulses received at one place is assumed to be K=1000. When a pulsed laser light of 40 kHz, for example, is used as an irradiation light, an image capturing time t is $6.25 \times 10^3$ (s)≈1.7 hours. As mentioned above, if a light quantity error is 30%, it is possible to reduce the light quantity error to about $30/\sqrt{1000} \approx 1\%$ by receiving the K=1000 pulses. Moreover, the number of times of the steps (the number of times of moving in the image capture regions) under this condition becomes $500 \times 500 = 2.5 \times 10^5$ times.

(Case 1): as shown in FIG. 4, it will be considered the case of using only the step and repeat operation of the stage. When the XYθ table 102 moves by a moving time 0.02 (s)/step, the moving time of the XYθ table 102 up to the time when the inspection of the whole inspection region has been finished is about $2.5 \times 10^5$ times×0.02≈1.4 hours. Therefore, adding the total moving time with the image capturing time, the inspection time can be 3.1 hours.

(Case 2): as shown in FIG. 5, it will be considered the case of optically performing step and repeat operation, specifically by moving the stage in the Y direction by the step and repeat operation, and using the scanning optical element in the X direction. It is assumed that the XYθ table 102 moves by a moving time 0.1 (s)/step, and each optical step time in the X direction is 0.01 (s). Assuming that the width of the inspection stripe 10 is 2 mm, scanning is performed in the X direction 10 times when capturing a certain inspection stripe 10. Therefore, the number of times of steps of the XYθ table 102 is(10 cm/2 mm)×(10 cm/0.2 mm)=$2.5 \times 10^4$ times. Moreover, the number of times of optical steps is $500 \times 500 = 2.5 \times 10^5$ times. The moving time of the XYθ table 102 up to the time when the inspection of the whole inspection region has been finished is 2500 (s). On the other hand, the sum of the optical step time is 2500 (s). Therefore, the total time of the moving time of the XYθ table 102 and the scanning time of the pulsed light source 151 up to the time when the inspection of the whole inspection region has been finished is about 1.4 hours. Therefore, added with the image capturing time, the inspection time can be 3.1 hours. That is, even if the moving time of the XYθ table 102 per step is prolonged, the total moving time can be shortened by means of combining with the optical step. That is, even if the moving speed of the XYθ table 102 per step is slow, the total moving time can be shortened by means of combining with the optical step.

Thus, by irradiating with the pulsed laser a predetermined times while the state of the stage is stopped, it becomes possible to suppress errors of measurement of each pixel, and to execute the inspection during a short time.

However, it is not restricted to the conditions mentioned above. First, for practical use, it is preferable to suppress a light quantity error to 5% or less. If it is assumed that the change of the light quantity of one pulse is 30% and the number of pulses is K, since the change of the light quantity by K times pulse irradiation is $30\%/\sqrt{K}$, it becomes necessary to perform K=36 times irradiation with the pulsed laser in order to make the change to 5%. That is, it is needed for each light receiving element 20 of the two-dimensional sensor array 105 to receive a pulsed light of about K=36 pulse. Using this condition as a premise, the practical use can be achieved even under the following condition. For example, it is assumed that the inspection region (measurement region) of the photomask 101 is 10 cm×10 cm, and the pixel size is 100 nm at the pitch p=100 nm. Then, there is used the two-dimensional sensor array 105 in which light receiving elements 20 (for example, photo-diodes) of (200 pieces in the length direction)×(200 pieces in the width direction) (X=200, Y=200) are arranged. In that case, the sensor region by the two-dimensional sensor array 105 is 0.02 mm×0.02 mm. For the sake of simplicity, the number of pulses received at one place is assumed to be K=50, for example. When a pulsed laser light of 40 kHz, for example, is used as an irradiation light, an image capturing time t is 8.68 hours. Although this is surely long as the image capturing time, if the light quantity error between pulses is 30%, it is possible to reduce the light quantity error to about $30/\sqrt{50} \approx 4.3\%$ by receiving the K=50 pulses. In the case 2 mentioned above, the number of times of the steps of the XYθ table 102 is (10 cm/2 mm)×(10 cm/0.02 mm)=$2.5 \times 10^5$ times. Moreover, the number of times of scanning of the pulsed light source 151 is (10 cm/0.02 mm)×(10 cm/0.02 mm)=$2.5 \times 10^7$ times. The moving time of the XYθ table 102 up to the time when the inspection of the whole inspection region has been finished is 25000 (s). On the other hand, the scanning time of the pulsed light source 151 is 25000 (s). Therefore, the total time of the moving time of the XYθ table 102 and the scanning time of the pulsed light source 151 up to the time when the inspection of the whole inspection region has been finished is about 14 hours. Therefore, added with the image capturing time, the inspection time becomes 22.57 hours.

As mentioned above, the pattern image focused on the two-dimensional sensor array 105 is photoelectrically converted by each light receiving element 20 of the two-dimensional sensor array 105, and further A/D (analog digital) converted by the sensor circuit 106.

The measurement data (optical image) output from the sensor circuit 106, after being stored in the stripe pattern memory 142 per inspection stripe 10, is sent to the comparison circuit 108 with the data indicating a position of the photomask 101 on the XYθ table 102 output from the position circuit 107. The measurement data is 8-bit unsigned data, for example, and expresses a gray level of the brightness of each pixel. The measurement data is sectioned per image data of 2000 pixels×2000 pixels, for example, and comparing is performed per pixel in the section.

As a reference image generation step, in the case of a die to database inspection, the reference circuit 112 first reads design data from the magnetic disk drive 109 through the control computer 110. Then, the read design data of the photomask 101 is converted into image data of binary values or multiple values to generate reference data (reference image). In the case of a die to die inspection, after measurement data (reference image) of a target workpiece to be referred to, which is captured with the target workpiece to be inspected, has been stored in the stripe pattern memory 142 per inspection stripe 10, the measurement data is sent to the comparison circuit 108 with data indicating the position of the photomask 101 on the XYθ table 102 output from the position circuit 107.

As a comparison step, position alignment between the measurement data and the reference data is first performed in the comparison circuit 108. The comparison circuit 108 serving as a comparing unit compares each pixel signal of the measurement data with a reference pixel signal of the reference data according to a predetermined algorithm, and judges existence of a defect based on the comparison result. Then, the comparison result is output to, for example, the magnetic disk drive 109, magnetic tape drive 115, FD 116, CRT 117, pattern monitor 118, or printer 119. Alternatively, it may be output to the outside.

Although the time period during the shutter being open is controlled by measuring the number of pulses in this Embodiment, it is not restricted thereto. For example, it is acceptable to simply control to open the shutter during the time for 1000 pulses. For example, in the case of the oscillation frequency of a pulsed laser being 40 kHz, what is necessary is just to make this time be (1/40 kHz)×1000=25 m seconds.

By virtue of the structure as mentioned above, the image in a large region can be captured at once. Therefore, even when a pulsed light is used as an irradiation light, the image capturing time can be reduced since the image of a large region is captured at a time. Then, the number of pulses for receiving lights can be increased by using the time saved by reducing the image capturing time. Therefore, even when the pulsed light source of short wavelength is used, increase of the inspection time can be suppressed. Furthermore, even when the pulsed light source of short wavelength is used, the light quantity error can be reduced.

As mentioned above, in the inspection method in which the stage is moved by the step and repeat operation, even when the pulsed light source of short wavelength is used, the light quantity error can be reduced.

As mentioned above, the pattern inspection apparatus 100 according to Embodiment 1 has the first function of measuring a light signal from a part to be measured, by using a sensor, by means of emitting pulsed lasers predetermined times or for a predetermined time period, while regarding that there is a predetermined relative positional relation between the part to be measured in the region of the target workpiece and the sensor composed of a plurality of light receiving elements two-dimensionally arrayed. Furthermore, the pattern inspection apparatus 100 according to Embodiment 1 has the second function of measuring light signals from all the regions to be measured in the target workpiece, by moving the measurement region. Then, by using the measured light signal, defects on the target workpiece can be identified.

Furthermore, when the pattern inspection apparatus 100 irradiates the part to be measured in the region of the target workpiece, the region to be measured in the target workpiece and the sensor mentioned above are relatively stopped to have the predetermined relative positional relation, in order to emit pulsed lasers predetermined times or for a predetermined time period.

Now, aberration and image distortion of the optical system of the inspection apparatus 100 will be supplementally described. By using an aspheric lens as the objective lens arranged in the magnifying optical system 104 between the photomask 101 and the two-dimensional sensor array 105, an optical system having sufficiently small aberration and image distortion can be structured. It is preferable for a shifted amount due to distortion of the objective lens to be 1/10 pixel or less, more preferably to be 1/64 pixel or less. The reason for this is a measurement error occurs because information on one pixel is distributed to two or more pixel sensors due to the shifted amount. If the shifted amount is 1/10 pixel or less, the error can be suppressed to be about 10% or less, and if the shifted amount is 1/64 pixel or less, the error can be suppressed to be about 1.6%. Such a small distortion can be obtained by replacing a spherical lens usually used as an objective lens by an aspheric lens. Therefore, it is suitable to use an aspheric lens for the objective lens arranged in the magnifying optical system 104. However, the optical system becomes expensive when an aspheric lens is used. Then, in the case that aberration and image distortion occur because of using a spherical lens and a shifted amount of a predetermined pixel or more (for example, a shifted amount of 1/10 pixel, or 1 pixel or more) is generated, the distortion can be corrected as mentioned below. By virtue of the correction below, it is also possible to use a spherical lens to hold down the cost of apparatus. The correcting is performed as follows when aberration occurs.

Figure 7:
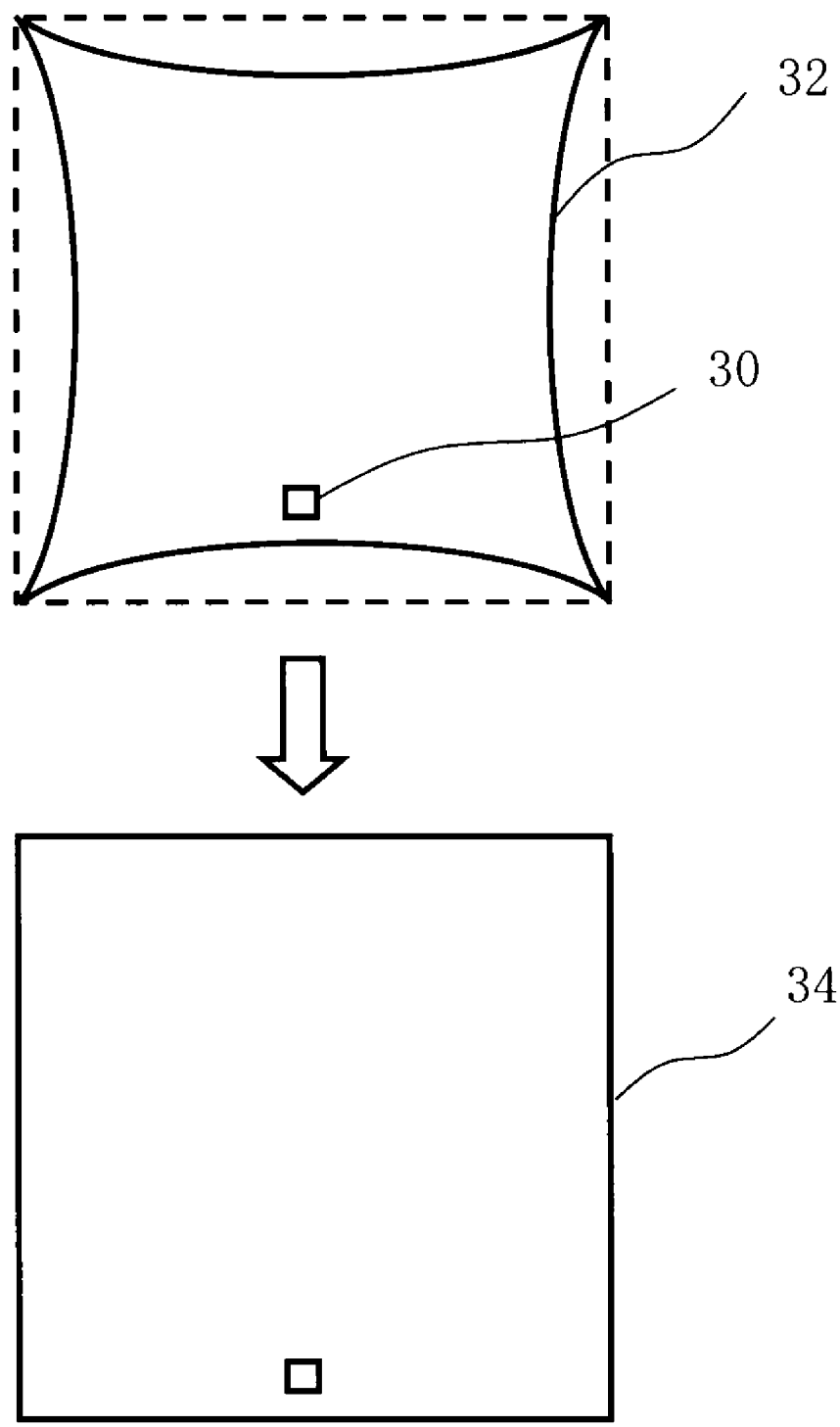
FIG. 7 shows a schematic diagram for illustrating a distortion correction described in Embodiment 1.

FIG. 7 shows a schematic diagram for illustrating a distortion correction described in Embodiment 1. When a measured image 32 obtained is distorted due to aberration as shown in FIG. 7, the position of a pixel 30 is also distorted. Then, by correcting the measured image 32 to be a corrected image 34, it becomes possible to correct the pixel position of the pixel 30 to be a desired position.

Figure 8:
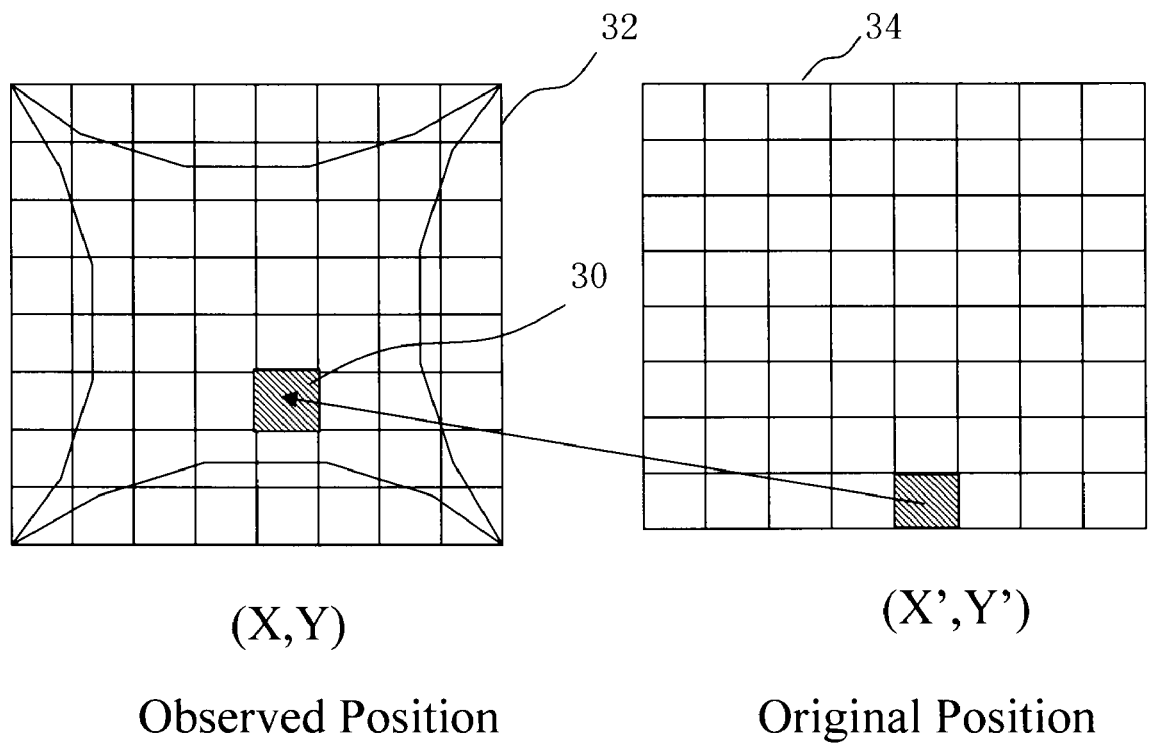
FIG. 8 shows a schematic diagram for illustrating a state of distortion described in Embodiment 1.

FIG. 8 shows a schematic diagram for illustrating a state of distortion described in Embodiment 1. It is assumed that the pixel 30 originally exists at the position (X', Y') on the target workpiece. Optical information on this pixel 30 is to be observed by a certain light receiving element 20, which is a pixel sensor at the position (X, Y) on the two-dimensional sensor array 105. The distortion of the optical system (more specifically, the distortion of the objective lens between the photomask 101 and the two-dimensional sensor array 105) distorts the relation between (X, Y) and (X', Y'). The relation is assumed to be expressed by the following equations (2-1) and (2-2).

$$X = a' + b'_1 \cdot X' + b'_2 \cdot Y' + c'_1 \cdot X'^2 + c'_2 \cdot X'Y' + c'_3 \cdot Y'^2 \quad (2\text{-}1)$$

$$Y = p' + q'_1 \cdot X' + q'_2 \cdot Y' + r'_1 \cdot X'^2 + r'_2 \cdot X'Y' + r'_3 \cdot Y'^2 \quad (2\text{-}2)$$

For example, simulation of an image is performed using pattern data (design data) which is an origin of the pattern formed on the photomask 101. It will be considered the case in which a simulated image is compared with an actually measured image in order to detect a defect. First, assuming that there is no distortion, a light quantity of each pixel is calculated by simulation. Then, using the above-mentioned equations (2-1) and (2-2), calculation is performed to obtain a position (X, Y) to which the position (X', Y') of each pixel has changed due to the distortion. If the corresponding relation between the position (X', Y') and the position (X, Y) is known, it is possible to obtain a light quantity of the pixel at the position (X', Y') by the light receiving element located at the position (X, Y) on the two-dimensional sensor array 105. Such calculation is performed in the sensor circuit 106.

Figure 9:
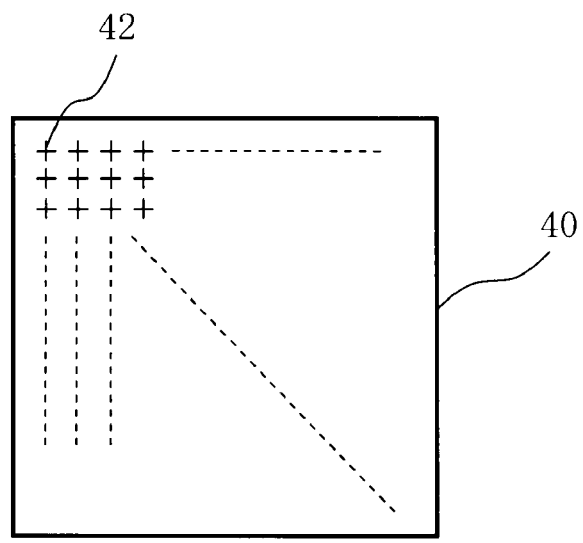
FIG. 9 shows an example of a test pattern described in Embodiment 1.
Figure 10:
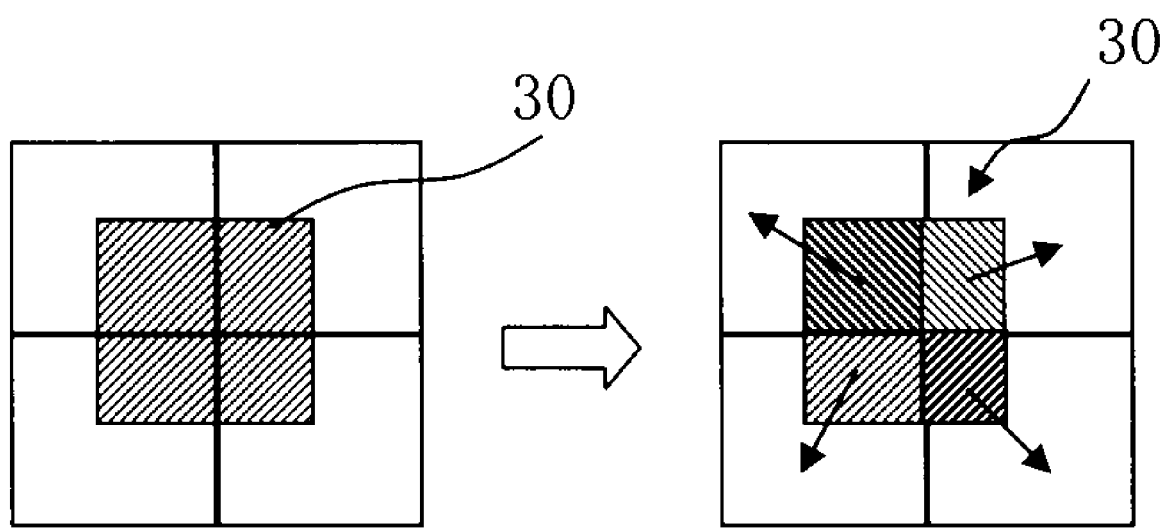
FIG. 10 illustrates a method of interpolating a light quantity described in Embodiment 1.

FIG. 9 shows an example of a test pattern described in Embodiment 1. First, it is necessary to create a test mask 40 in which a plurality of marks 42 having a predetermined interval each other are formed. Then, the position of each mark 42 in the test mask 40 is inspected by the inspection apparatus 100. Thereby, the amount of distortion due to aberration can be obtained. By approximating (fitting) the positions before and after the distortion by using the equations (2-1) and (2-2), each of the coefficients a' to r'$_3$ is calculated. Then, the obtained coefficients a' to r'$_3$ are set in the sensor circuit 106. The sensor circuit 106, using the equations (2-1) and (2-2) in which the coefficients a' to r'$_3$ are set, just corrects distortion of data of the measured image obtained from the photomask 101 used as a target workpiece to be actually inspected. The sensor circuit 106 is an example of a correction unit. By virtue of this correction, the amount of distortion due to aberration can be excluded when comparing is performed by the comparison circuit 108, thereby increasing the inspection precision. Moreover, there may be a case where, because of the distortion, the original pixel extends over pixels because it cannot be accommodated within the pixel region having been distorted. In such a case, it is preferable to interpolate as follows:

FIG. 10 illustrates a method of interpolating a light quantity described in Embodiment 1. In FIG. 10, if the original pixel after being distorted extends over pixels, what is necessary is just to divide the light quantity according to a ratio of areas divided at the boundary between pixels, and to distribute the divided light quantity to the light receiving element corresponding to each pixel.

Regarding FIG. 2, although it has been described the two-dimensional sensor array 105 in which a plurality of light receiving elements 20 are two-dimensionally arrayed in the X direction and the Y direction, the array method is not restricted to this case.

Figure 11:
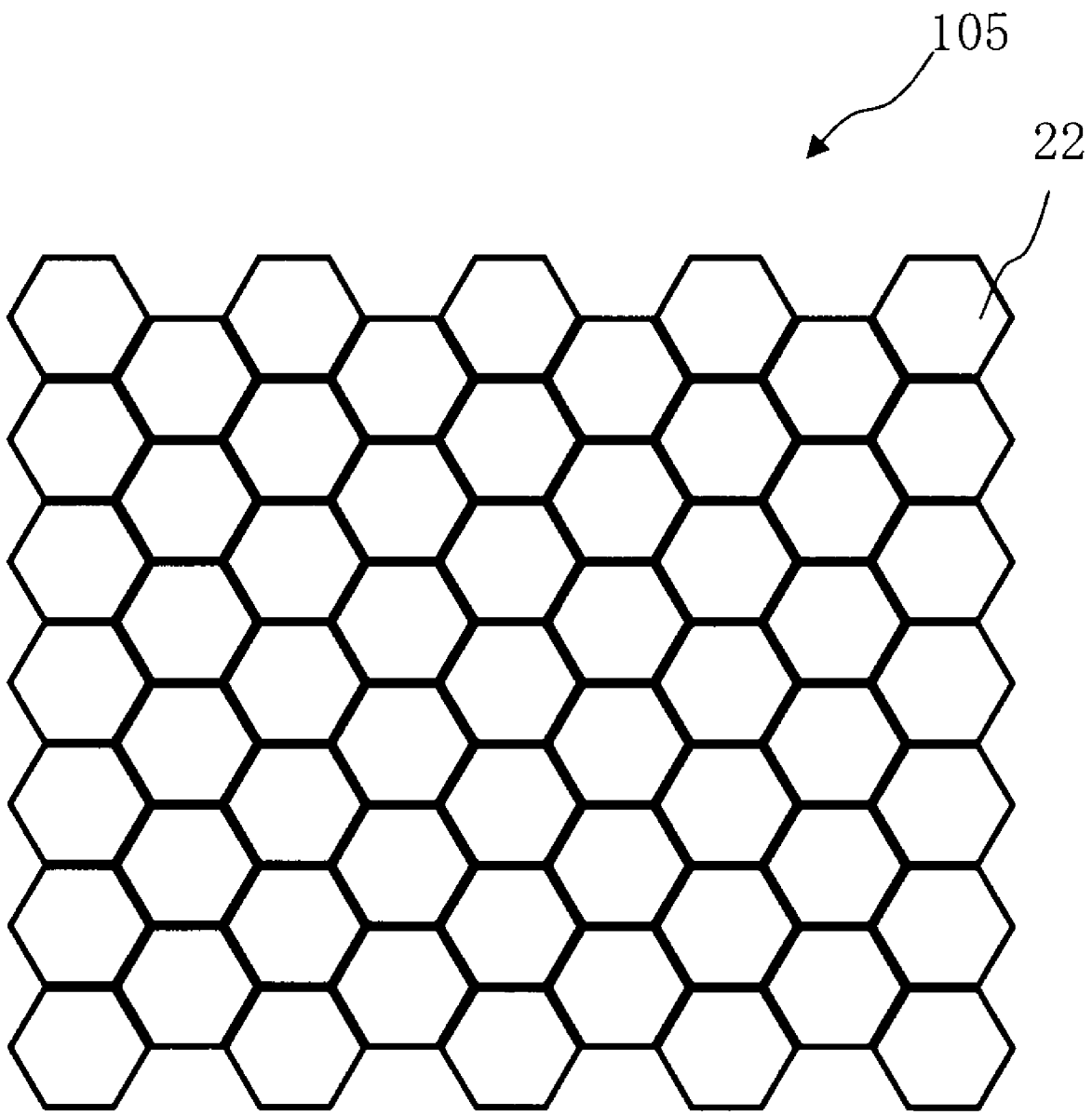
FIG. 11 shows another example of an array state of the two-dimensional sensor array described in Embodiment 1.

FIG. 11 shows another example of an array state of the two-dimensional sensor array described in Embodiment 1. For example, as shown in FIG. 11, it is also preferable to form each light receiving element 22 to be a hexagon and to arrange a plurality of them to contact their sides each other.

Embodiment 2

In the above Embodiment 1, the case of capturing an image by a step and repeat method has been described. In the present Embodiment 2, the case of capturing an image while continuously moving the XYθ table 102 will be described.

Figure 12:
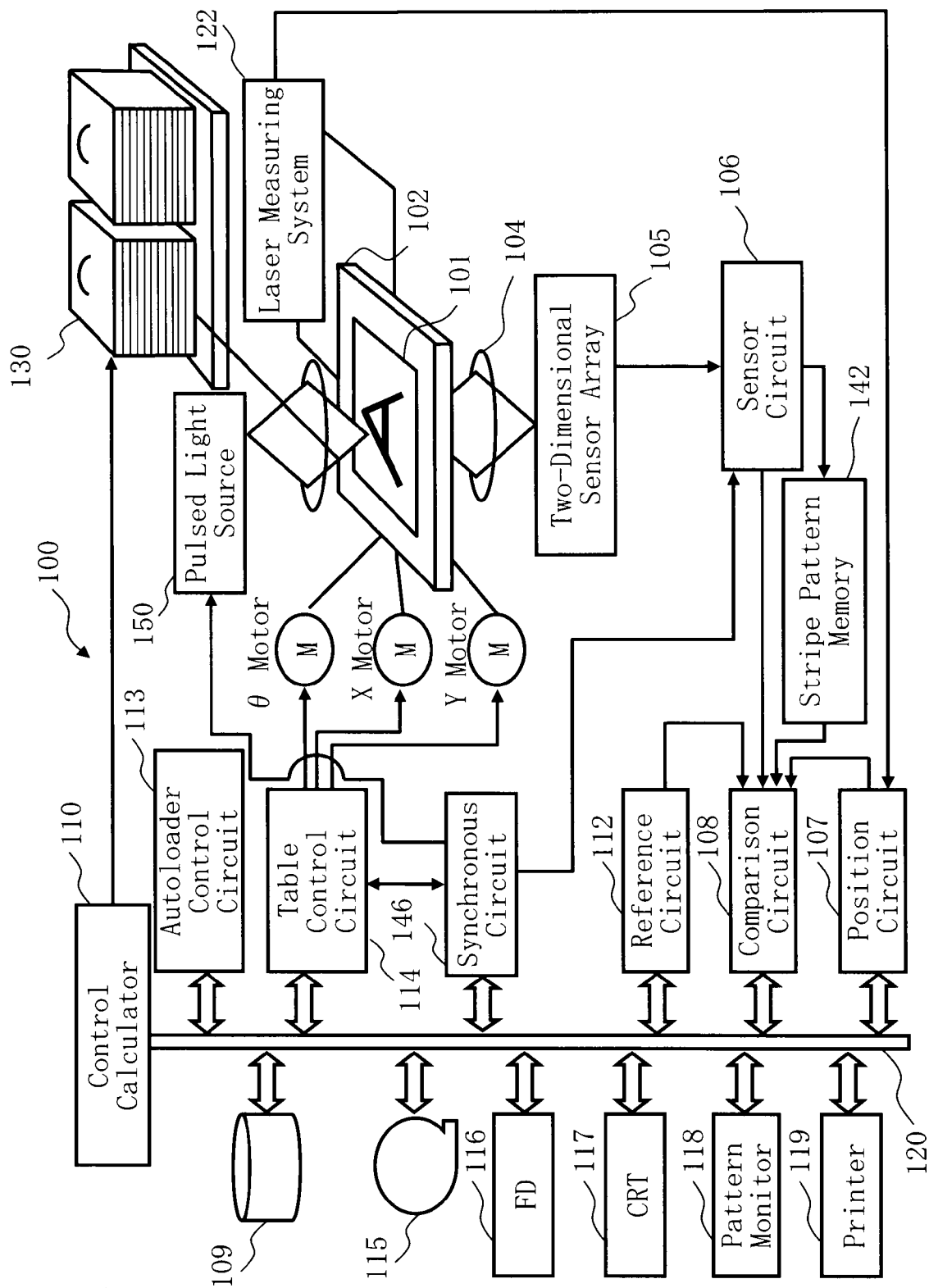
FIG. 12 shows a schematic diagram illustrating a structure of a pattern inspection apparatus described in Embodiment 2.

FIG. 12 shows a schematic diagram illustrating a structure of a pattern inspection apparatus described in Embodiment 2. In FIG. 12, structure elements are the same as those in FIG. 1 except for that a synchronous circuit 146 is arranged instead of the shutter 152, the optical sensor 153, and the pulse controller 140. FIG. 12 depicts structure elements necessary for describing Embodiment 2, and it should be understood that other structure elements generally necessary for the target workpiece inspection apparatus 100 may also be included therein. For the sake of simplicity, it is assumed that an aspheric lens is used in the optical system and there is neither aberration nor distortion.

Figure 13:
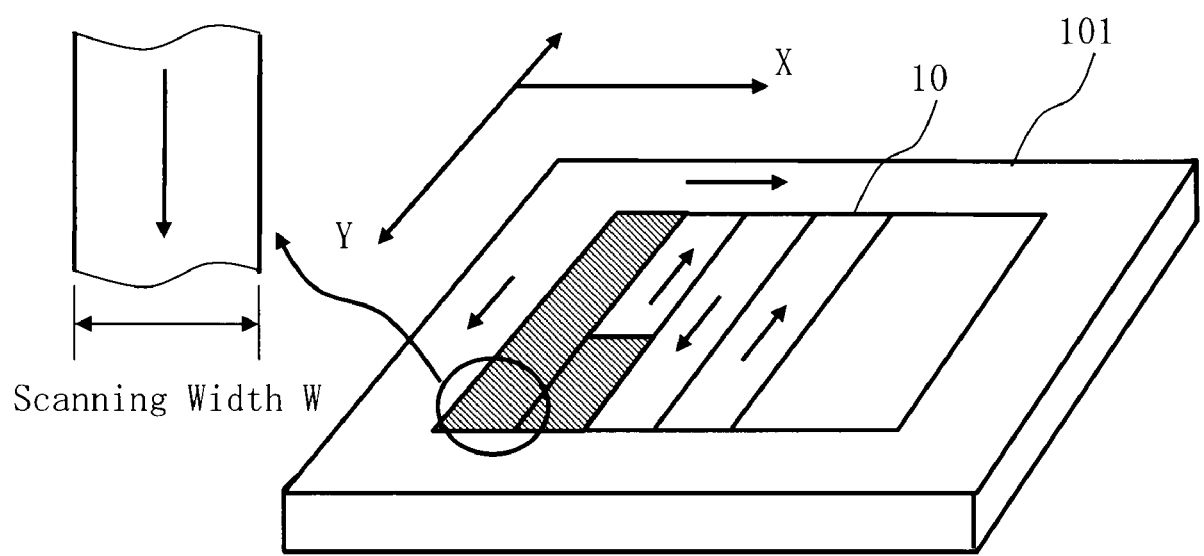
FIG. 13 shows a schematic diagram for illustrating a step of acquiring an optical image described in Embodiment 2.

FIG. 13 shows a schematic diagram for illustrating a step of acquiring an optical image in Embodiment 2. As shown in FIG. 13, a region to be inspected of the photomask 101 is virtually divided into a plurality of strip-like inspection stripes 10, each having a scanning width W in the X direction. The movement of the XYθ table 102 is controlled so that each of the divided inspection stripes 10 can be continuously scanned. An optical image is acquired while the XYθ table 102 is moving in the Y direction. In the two-dimensional sensor array 105, an image having the scanning width W as shown in FIG. 13 is input continuously. After acquiring the image on the first inspection stripe, an image having the scanning width W on the second inspection stripe is input, while the XYθ table 102 is moving in the direction reverse to the above. Then, in the case of acquiring an image on the third inspection stripe, the image is acquired while the XYθ table 102 is moving in the direction reverse to the one for acquiring the image on the second inspection stripe, i.e., moving in the same direction as the one for acquiring the image on the first inspection stripe.

Figure 14:
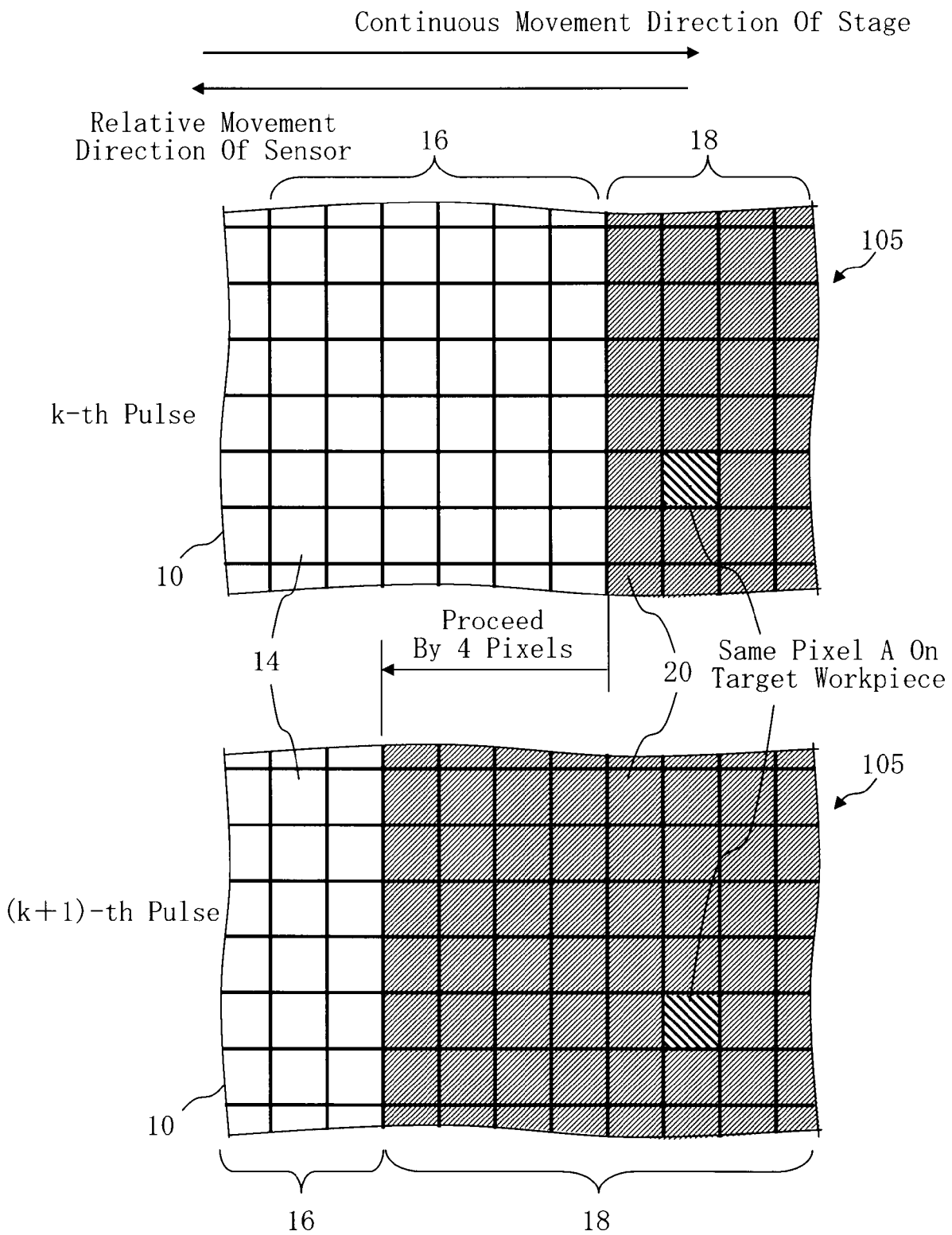
FIG. 14 shows another schematic diagram for illustrating a step of acquiring an optical image described in Embodiment 2.

FIG. 14 shows another schematic diagram for illustrating a step of acquiring an optical image in Embodiment 2. FIG. 14 shows the case where the X-direction width W of the inspection stripe 10 is set to be equivalent to the array width of the light receiving element in the X direction of the two-dimensional sensor array 105. For example, there is used the two-dimensional sensor array 105 where the light receiving elements 20 for 2000×2000 pixels are arranged. The XYθ table 102 moves continuously so that a predetermined number of pixels may be shifted between pulses of a pulsed light.

First, the XYθ table 102 is moved to just before the starting position of capturing an image of a stripe to be inspected. Then, the stage is accelerated, and when the image capturing region goes into the inspection region, the stage is made to keep moving at a predetermined fixed speed. Simultaneously, as an irradiation step, a signal is sent from the synchronous circuit, and the pulsed light source 150 emits a pulsed light. The continuous movement speed of the XYθ table 102 at this time is a speed at which a predetermined number of pixels shift in the Y direction between pulses of a pulsed light, wherein the predetermined number of pixels is a number of natural number times one pixel: four pixels in the example in FIG. 14, for example. This is performed by that the synchronous circuit 146 acquires position information on the stage measured by the laser measuring system, via the position circuit 107, and sends a signal which directs to emit, to the pulsed light source 150 based on the position. At this time, as an image capture step performed simultaneously with the pulsed laser irradiation, the two-dimensional sensor array 105 captures a pattern image in a two-dimensional image capture region 18 of the photomask 101 which is irradiated with the pulsed beam. Specifically, while the XYθ table 102 is continuously moving, an image in the two-dimensional image capture region 18 is captured with a pulsed laser of the k-th pulse. Furthermore, the XYθ table 102 continues moving at a fixed speed. When a predetermined number of pixels have moved by the fixed speed movement, irradiation is performed by using a pulsed laser of the (k+1)-th pulse, and an image in the two-dimensional image capture region 18 is captured. The example of FIG. 14 shows the case where the two-dimensional image capture region 18 proceeds to a non-capture region 16 side by 4 pixels.

Figure 15:
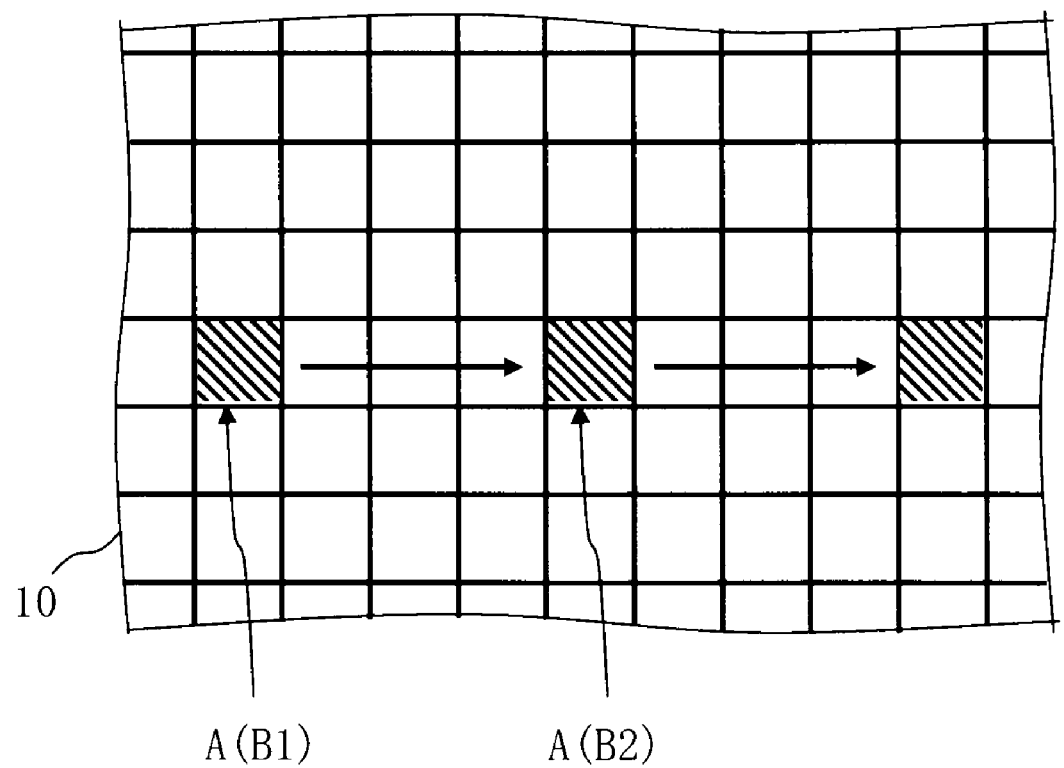
FIG. 15 shows a situation of movement of a pixel in FIG. 14 seen from the two-dimensional sensor array side.

FIG. 15 shows a situation of movement of the pixel in FIG. 14, seen from the two-dimensional sensor array side. For example, information on a certain pixel A on the target workpiece is measured by a light receiving element B1 being the k-th pulse irradiation, by a light receiving element B2, which is the next but three, being the (k+1)-th pulse irradiation, and by a next light receiving element, which is the next but three from the light receiving element B2, being the (k+2)-th pulse irradiation. The measuring is repeated like the above. The light quantity of the pixel A is measured at the times of (the number of light receiving elements in the movement direction)/(the number of pixels which move between pulses), that is (2000)/(4)=500 times. Corresponding to this, the two-dimensional sensor array 105 performs accumulative addition of all the optical information (light quantity) from the pixel A, as shown in the following equation (3):

all light quantity from pixel $A$=light quantity obtained by light receiving element $B1$ at $k$-th pulse irradiation+light quantity obtained by light receiving element $B2$ at $(k+1)$-th pulse irradiation+light quantity obtained by light receiving element $B3$ at $(k+2)$-th irradiation+ . . . and so on. (3)

An example of the two-dimensional sensor array 105 which performs such an operation and controlling thereof will be described below. The two-dimensional sensor array 105 is almost the same as the conventional TDI sensor. The two-dimensional sensor array 105 has a structure to be given a shift amount of a pixel position from the outside. When the shift amount is given, the two-dimensional sensor array 105 moves all the measured light quantity information stored in each internal light receiving element (in the direction of the stage continuous movement) to a light receiving element which is away by the shift amount indicated from the outside. For example, when 4 is given as the shift amount, the measured light quantity information stored in the light receiving element B1 of FIG. 15 is moved to B2. Similarly, measured light quantity information stored in other light receiving element is also moved to a light receiving element which is the next but three. At this time, measured light quantity information stored in the light receiving elements existing in the last n-th row in the direction of movement of measured light quantity, (in the above example, 2000 pixels/row×4 rows=8000 pixels) is output outside.

The controlling method using the two-dimensional sensor array 105 is performed as follows: It is assumed that the shift amount of a pixel is 4 and the sensor is composed of 2000× 2000 light receiving elements. The synchronous circuit 146 recognizes that the stage has reached a predetermined position, and directs the pulsed light source 150 to emit lights. Then, the pulsed light source 150 emits a pulsed laser to irradiate the photomask 101, and the two-dimensional sensor array 105 measures the quantity of the light. Immediately after that, the synchronous circuit 146 sends the shift amount "4" to the two-dimensional sensor array 105. In response to receiving, the two-dimensional sensor array 105 moves measured light quantity information stored in each light receiving element to the light receiving element next but three. Moreover, the two-dimensional sensor array 105 outputs the measured light quantity information stored in the light receiving elements of 8000 pieces in the last four rows. The measured light quantity information is sent to the comparison circuit to be used for inspecting defects. In this case, the operation speeds of the two-dimensional sensor array 105 and the signal transmission system are set so that all the operations, from giving a shift amount to the two-dimensional sensor array 105 until all the light quantity information for the last four rows having been output by the two-dimensional sensor array 105, may finish within the period (0.025 second in the case of 40 kHz oscillation) of a pulsed laser. By keeping such a speed, irradiation with a pulsed laser is not performed during the period from giving a shift amount to the two-dimensional sensor array 105 until all the light quantity information for the last four rows having been output. That is, each light receiving element of two-dimensional sensor array 105 does not measure a new light quantity. Then, detecting that the XYθ table 102 has moved by 4 pixels, the synchronous circuit 146 directs the pulsed light source 150 to emit lights. The pulsed light source 150 emits lights, and the two-dimensional sensor array 105 measures the light quantity of each pixel from the photomask 101. By repeating the above, as shown in the equation (3), the quantity of light in each pixel is measured to be used for inspection.

By performing the above, it is possible to acquire the total light quantity of the pixel group obtained by irradiation of 500 times with the pulsed laser. As mentioned above, the two-dimensional sensor array 105 outputs information of the accumulative addition, once per pulse, for the pixels of 2000 pixels/row×four rows. Then, the output data is sent to the comparison circuit 108 to be used for inspecting defects. By virtue of 500 times irradiation and measurement of the pulsed laser per pixel, the error of the light quantity can be suppressed to 30%/√(500)=1.34%.

Other examples of the two-dimensional sensor array 105 and controlling thereof will be described below. The operation of the two-dimensional sensor array 105 is similar to the above-mentioned example. It is structured so that a command signal C may be given to the two-dimensional sensor array 105 from the outside. Receiving this command signal C, the two-dimensional sensor array 105 moves every measured light quantity information stored in each light receiving element to the light receiving element next but one in the direction of the continuous movement of the stage. Moreover, at this time, the measured light quantity information stored in the light receiving elements existing in the last row (for 2000 pixels in the above example) in the direction of moving the measured light quantity of the two-dimensional sensor array 105 is output outside. When finishing outputting outside, the two-dimensional sensor array 105 sends a signal indicating that the outputting has finished to the outside.

The controlling method using the two-dimensional sensor array 105 is performed as follows: It is assumed that the shift amount of a pixel is 4 and the two-dimensional sensor array 105 is composed of 2000×2000 light receiving elements. The synchronous circuit 146 recognizes that the stage has reached a predetermined position, and directs the pulsed light source 150 to emit lights. Then, the pulsed light source 150 emits a pulsed laser to irradiate the mask, and the two-dimensional sensor array 105 measures the quantity of the light. In other words, the synchronous circuit 146 sends the signal directing the light emission to the light source in accordance with the position of the stage. Immediately after that, the synchronous circuit 146 sends the command signal C to the sensor. In response to receiving this command signal C, the two-dimensional sensor array 105 moves measured light quantity information stored in each light receiving element to the light receiving element next but one in the direction of the continuous movement of the stage. Moreover, the two-dimensional sensor array 105 outputs the measured light quantity information stored in the light receiving elements of 2000 pieces in the last row. The measured light quantity information is sent to the comparison circuit 108 to be used for inspecting defects. After outputting the measured light quantity information for the 2000 pieces, the two-dimensional sensor array 105 sends an end signal indicating that the outputting has finished to the synchronous circuit 146. Receiving this end signal, the synchronous circuit 146 sends the command signal C again to the two-dimensional sensor array 105. Then, the two-dimensional sensor array 105 performs moving and outputting the measured light quantity information, and sends the end signal to the two-dimensional sensor array 105. Repeating such operations, exchanging of the command signal C and the end signal is performed four times. By performing the above, measured light quantity information stored in a light receiving element in the two-dimensional sensor array 105 is moved to the light receiving element next but three in the direction of continuous movement of the stages. Moreover, the measured light quantity information stored in the last four rows at the end in the direction of continuous movement of the stage, is sent to the comparison circuit 108 to be used for inspecting defects. In this case, the operation speeds of the two-dimensional sensor array 105 and the signal transmission system are set so that all the operations, from the synchronous circuit 146's giving the first command signal C to the sensor after the irradiation with one pulse laser until the two-dimensional sensor array 105's outputting all the light quantity information for the last four rows, may finish within the period (0.025 second in the case of 40 kHz oscillation) of the pulsed laser. That is, the two-dimensional sensor array 105 finishes outputting the light quantity information on a predetermined number of pixel rows (pixels in a two-dimensional region corresponding to the predetermined number of pixels of the pattern image) captured, within the period of the pulsed light. Since the light receiving elements are two-dimensionally arrayed in the two-dimensional sensor array 105, the light receiving elements are arranged also in a line perpendicular to the direction of the stage movement. Therefore, light quantify information of (the number of shifted pixels)×(the number of pixels arrayed perpendicularly to the shifting direction) is the light quantity information for the pixel rows. By keeping such a speed, irradiation with a pulsed laser is not performed during the period, after irradiation with one pulse laser, from the synchronous circuit 146's sending the first command signal C to the two-dimensional sensor array 105 to give a shift amount until the two-dimensional sensor array 105's outputting all the light quantity information for the last four rows. Then, detecting that the XYθ table 102 has moved by 4 pixels, the synchronous circuit 146 directs the pulsed light source 150 to emit lights. The pulsed light source 150 emits lights, and the two-dimensional sensor array 105 measures light quantity of each pixel from the target workpiece. By repeating the above, as shown in the equation (3), the quantity of light in each pixel is measured to be used for inspection.

An example of computation of inspection time will be described below. It is assumed that the inspection region (measurement region) of the photomask 101 is L×L (cm), and the pixel size is p×p (nm). Then, there is used the two-dimensional sensor array 105 in which (X light receiving elements 20 in the X direction)×(Y light receiving elements 20 in the Y direction) are arranged. Moreover, it is assumed that the number of pulses received at one place is K. K=1 in Embodiment 2. The number of pixels to be shifted is S. When a pulsed laser light of N (kHz), for example, is used as an irradiation light, the image capturing time t (s) can be calculated by the following equation (4).

$$t = K \cdot L^2 \cdot 10^{11}/(p^2 \cdot N \cdot X \cdot S) \quad (4)$$

Similarly to Embodiment 1, it is assumed that, for example, the inspection region (measurement region) of the photomask 101 is 10 cm×10 cm, and the pixel size is 100 nm at the pitch p=100 nm. Then, there is used the two-dimensional sensor array 105 in which light receiving elements 20 (for example, photo-diodes) of (2000 pieces in the length direction)×(2000 pieces in the width direction) (X=2000, Y=2000) are arranged. When the stage proceeds by 4 pixels between pulses under this condition, light quantity of 500 pulses is accumulated in each light receiving element 20. Therefore, it is possible to reduce the light quantity error to about $30/\sqrt{500} \approx 1.3\%$. Then, when a pulsed laser light of 40 kHz is used as an irradiation light, the image capturing time t becomes 0.87 hours.

In order to inspect a certain frame and to further inspect the following frame, time for step movement of moving the stage in the direction perpendicular to the continuous movement is needed for achieving the inspection. However, such a time is so short that it can be disregarded compared with the image capturing time. This can be described as follows: The width (width in the direction perpendicular to the stage continuous movement) of the frame is 200 μm=0.2 mm, and the number of the frames is 500. If time for step movement of moving the stage to the next frame after having inspected a certain frame is 0.1 seconds, all the time for the step movement becomes 50 seconds. Thus, when performing the inspection while continuously moving the stage, the time of the step movement is so short that it can be disregarded compared with all the inspection time.

Moreover, when the stage proceeds by 2 pixels between pulses under this condition, the light quantity of 1000 pulses will be accumulated in each light receiving element 20. Therefore, the light quantity error can be suppressed to about $30/\sqrt{1000} \approx 0.95\%$. When a pulsed laser light of 40 kHz is used as an irradiation light, the image capturing time t becomes 1.76 hours. Moreover, when the stage proceeds by 1 pixel between pulses under this condition, the light quantity of 2000 pulses will be accumulated in each light receiving element 20. Therefore, the light quantity error can be suppressed to about $30/\sqrt{2000} \approx 0.67\%$. When a pulsed laser light of 40 kHz, for example, is used as an irradiation light, the image capturing time t becomes 3.47 hours.

When based on the premise that the light quantity error is suppressed to 5% or less, what is necessary for each light receiving element 20 is to accumulate a light quantity of 50 pulses. Therefore, there is used the two-dimensional sensor array 105 in which light receiving elements 20 of (1000 pieces in the length direction)×(50 pieces in the width direction) (that is, X=1000, Y=50) are arrayed. When the stage proceeds by 1 pixel between pulses under this condition, if a pulsed laser light of 40 kHz, for example, is used as an irradiation light, the image capturing time t becomes 6.9 hours.

Similarly, when based on the premise that the light quantity error is suppressed to 5% or less, what is necessary for each light receiving element 20 is to accumulate light quantity of 50 pulses. Therefore, the stage may proceed by 20 pixels between pulses by using the two-dimensional sensor array 105 in which light receiving elements 20 of (100 pieces in the length direction)×(1000 pieces in the width direction) (that is, X=100, Y=1000) are arrayed. When a pulsed laser light of 40 kHz, for example, is used as an irradiation light under this condition, the image capturing time t becomes 3.47 hours.

Similarly, when based on the premise that the light quantity error is suppressed to 5% or less, what is necessary for each light receiving element 20 is to accumulate light quantity of 50 pulses. Therefore, the stage may proceed by 2 pixels between pulses by using the two-dimensional sensor array 105 in which light receiving elements 20 of (100 pieces in the length direction)×(100 pieces in the width direction) (that is, X=100, Y=100) are arrayed. When a pulsed laser light of 40 kHz, for example, is used as an irradiation light under this condition, the image capturing time t becomes 34.7 hours. Thus, it becomes possible to suppress a measurement error of each pixel by controlling the timing between the stage position control based on a stage moving speed control and the irradiation by a pulsed laser.

As mentioned above, errors of measurement can be reduced by continuously moving the stage so that it may shift by a predetermined number of pixels (that is the number of pixels of natural number times one pixel) between pulses of pulsed lights. Measuring time can be greatly reduced especially by making the value of the number of pixels to be shifted be 2 or more like an example mentioned above. As the background of this reduction, although irradiation of only one pulse is performed at each stage position, by virtue of having sufficient number of light receiving elements in the direction of the stage movement, the number of irradiation with a pulsed laser for one pixel can be increased to reduce measurement errors. As the reason for this reduction, by virtue of making the value of the number of pixels to be shifted between pulses be 2 or more, the direct linkage between the pixel size itself and the stage movement speed has been eliminated. That is, if only one pixel is shifted between pulses, the stage can proceed by only one pulse between pulses. However, if two pixels or more are shifted, it becomes possible to make the stage movement speed twice or more. At this time, although the times of measurement per pixel decreases, since the number of the light receiving elements in the direction of the stage continuous movement has been secured, degradation of measurement precision can be suppressed to an allowable level. This method will be more effective in the future when the size of a pixel is made smaller in order to increase the precision of judging defects. For example, when the pixel size is changed from 100×100 nm to 50×50 nm or 25×25 nm, if the stage can move by only 1 pixel between pulses, the stage speed becomes ½ or ¼, respectively. Corresponding to this, inspection time will become twice and four times, respectively. On the other hand, according to the method of shifting by 2 pixels or more, in the former case, it is possible to make the stage speed and the measuring time be the same as those in the case of the pixel size of 100×100 nm by shifting by 2 pixels between pulses. In the latter case, it is possible to make the stage speed and the measuring time be the same as those in the case of the pixel size of 100×100 nm by shifting by 4 pixels between pulses. Thus, even if the pixel size is made small, it is possible to suppress the increase in measuring time by the method of shifting by 2 pixels or more.

According to Embodiment 2, since it is necessary to synchronize the irradiation timing of a pulsed light with the sensor circuit 106 which processes a signal from the two-dimensional sensor array 105, the synchronous circuit 146 controls the emission of lasers to be in accordance with the position of the stage in the example above mentioned. However, the control of the timing is not restricted to this method. Even when the pulsed laser light source oscillates automatically, it is acceptable to interlock the oscillation of a pulsed laser with the speed of the stage continuous movement speed by way of sending a signal, which indicates that oscillation has been performed, to the synchronous circuit 146 from the light source, and controlling the stage speed by the synchronous circuit 146. Alternatively, it is also acceptable to interlock the oscillation of a pulsed laser with the speed of the stage continuous movement speed by way of detecting a pulse emission by the optical sensor, sending it to the synchronous circuit 146 and controlling the stage speed by the synchronous circuit 146.

In the structure of FIG. 12, although a signal is output to the pulsed light source 150 from the synchronous circuit 146, it is not restricted to this. It is also preferable to transmit a signal to the synchronous circuit 146 from the pulsed light source 150 at every oscillation.

The operations of the inspection apparatus 100 from outputting measurement data (optical image) from the sensor circuit 106 to outputting an inspection result by the comparison circuit are the same as those in Embodiment 1. Moreover, the methods of correcting distortion, arranging the light receiving element of the two-dimensional sensor array 105, etc. which are not explained in Embodiment 2 are the same as those of Embodiment 1.

As mentioned above, the pattern inspection apparatus 100 according to Embodiment 2 has the first function of measuring a light signal from a part to be measured, by using a sensor, by means of emitting pulsed lasers predetermined times or for a predetermined time period, while regarding that there is a predetermined relative positional relation between the part to be measured in the region of the target workpiece and the sensor composed of a plurality of light receiving elements two-dimensionally arrayed. Furthermore, the pattern inspection apparatus 100 according to Embodiment 2 has the second function of measuring light signals from all the regions to be measured in the target workpiece, by moving a measurement region. Then, by using the measured light signal, defects on the target workpiece can be identified.

The pattern inspection apparatus 100 measures the quantity of light from the target workpiece while continuously moving the stage. Irradiation with a pulsed laser is performed only once at a predetermined positional relation when there is the predetermined positional relation between a part to be measured in the region of the target workpiece and the sensor. The continuous movement of the stage is set so that it may shift by a predetermined number of pixels (the number of pixels of natural number times one pixel) between pulses.

As described in Embodiment 1, by using an aspheric lens as the objective lens arranged at the magnifying optical system 104 between the photomask 101 and the two-dimensional sensor array 105, it is possible to structure an optical system in which aberration and image distortion are sufficiently small. It is preferable for the shifted amount due to distortion of the objective lens to be 1 pixel or less, more preferably to be 1/64 pixel or less. Such a small distortion can be obtained by replacing a spherical lens usually used as an objective lens by an aspheric lens having less distortion. Therefore, using an aspheric lens is suitable for the objective lens arranged in the magnifying optical system 104, and however, the optical system becomes expensive when an aspheric lens is used. Meanwhile, when a spherical lens is used, aberration and image distortion will occur.

In the case there is distortion, optical distortion correction may be performed to be used for inspection. In that case, it may be acceptable, after acquiring image information of each pulse, as explained in Embodiment 1, to create an optical image whose distortion has been corrected for the acquired image information, which is performed for all the image information of each pulse, and then, based on obtained image information, to calculate a light quantity of each pixel by using the equation (3) in order to judge a defect based on the calculated result. It will be concretely described below.

Figure 16:
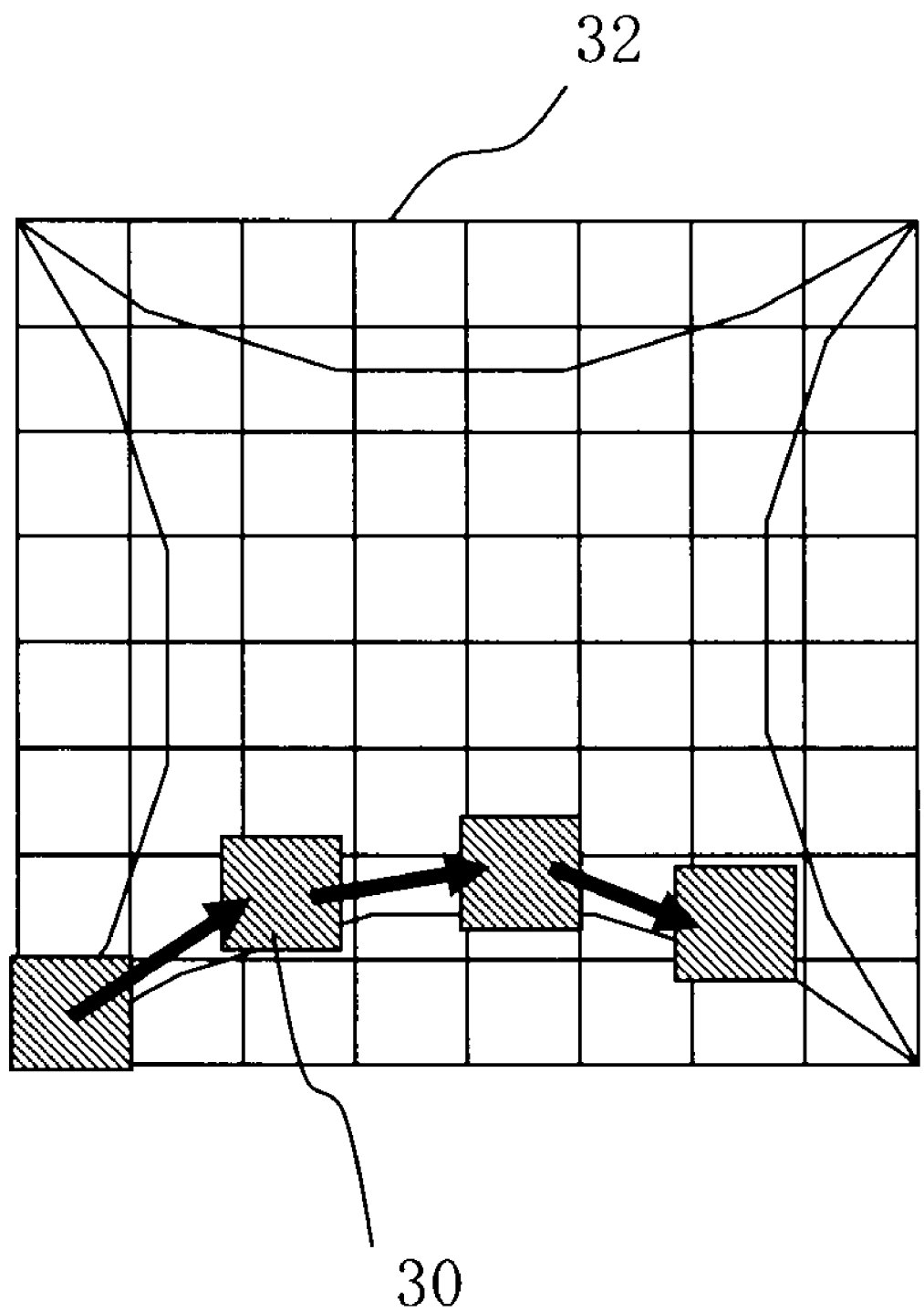
FIG. 16 shows a schematic diagram for explaining a state of distortion described in Embodiment 2.

FIG. 16 shows a schematic diagram for explaining a state of distortion described in Embodiment 2. Now, a certain pixel 30 will be described concretely. The light quantity of this pixel is measured while the stage is continuously moving. When seen on the two-dimensional sensor array 105, the pixel 30 moves on a curved line due to distortion of the objective lens as shown in FIG. 16. That is, pixels on the target workpiece do not move linearly on the two-dimensional sensor array 105. If the amount shifted from the straight line corresponds to the amount of one pixel or more of the light receiving element, it means that the light quantity of this pixel will be distributed to two or more pixels. By this, light quantity information is distributed, thereby deteriorating the detection precision. Therefore, it is preferable for the amount shifted from the straight line due to distortion of the objective lens to be one pixel or less, more preferably to be 1/64 pixel or less. In the case that a shifted amount of a predetermined pixel number or more (for example, one pixel or more) is generated because of aberration and image distortion produced by using a spherical lens, correcting will be performed as described below. By virtue of correcting, a spherical lens can be used, which suppresses the cost of the apparatus. When aberration occurs, it will be corrected as follows:

Although the case of using a TDI sensor as the two-dimensional sensor array 105 is described in the example mentioned above, when correcting distortion, an area sensor is used instead of the TDI sensor. The sensor circuit 106 loads acquired data of all the light receiving elements, which are two-dimensionally arranged, per pulse. The sensor circuit 106 computes data when there being no distortion, from the data loaded by the light receiving element based on irradiation of one pulse. It is assumed that the pixel 30 originally exists at the position (X', Y') on the target workpiece, and optical information on this pixel 30 is to be observed by the light receiving element 20 at the position (X, Y) on the two-dimensional sensor array 105. The relation between (X, Y) and (X', Y') effected by the distortion can be expressed as the following equations (5-1) and 5-2).

$$X' = a + b_1 \cdot X + b_2 \cdot Y + c_1 \cdot X^2 + c_2 \cdot XY + c_3 \cdot Y^2 \quad (5\text{-}1)$$

$$Y' = p + q_1 \cdot X + q_2 \cdot Y + r_r \cdot X^2 + r_2 \cdot XY + r_3 \cdot Y^2 \quad (5\text{-}2)$$

Then, the position of each mark 42 in the test mask 40 shown in FIG. 9 is inspected by the inspection apparatus 100. Thereby, the amount of distortion due to aberration can be obtained. By approximating (fitting) the positions before and after the distortion by using the equations (5-1) and (5-2), each of the coefficients a to $r_3$ is calculated. Then, the obtained coefficients a to $r_3$ are set in the sensor circuit 106.

How to make the position of a pixel whose light quantity has been measured correspond to the position of a pixel in the case of no distortion is determined based on the equations (5-1) and (5-2). Thereby, it is possible to compute a light quantity of each pixel having no distortion. As mentioned above, the sensor circuit 106 corrects distortion of data of the measured image obtained from the photomask 101 used as a target workpiece to be actually inspected. The sensor circuit 106 is an example of a correction unit.

Moreover, when applying the measured pixel to a pixel without distortion, as shown in FIG. 10, there is a case in which the position of the measured pixel extends over some pixels without distortion. In that case, as shown in FIG. 10, the light quantity is divided in accordance with the area ratio divided by the boundary of pixels, and the light quantity is distributed into light quantities stored the light receiving elements corresponding to each pixel based on the areas relating to pixels without distortion.

Then, using the equation (3), accumulative addition is performed for the light quantity data of corrected pixels, a predetermined number of times of pulses. By virtue of this, data of light quantity of each pixel in the case of no distortion can be acquired as the one obtained by pulse irradiation of the predetermined times.

As mentioned above, even when a pulsed light source of short wavelength is used in the inspection method of continuously moving the stage, it is possible to reduce light quantity errors. can be reduced.

Embodiment 3

In the above Embodiment 2, the case in which the stage moves at a fixed speed has been described. In the present Embodiment 3, the case of the stage speed being variable will be described.

Figure 17:
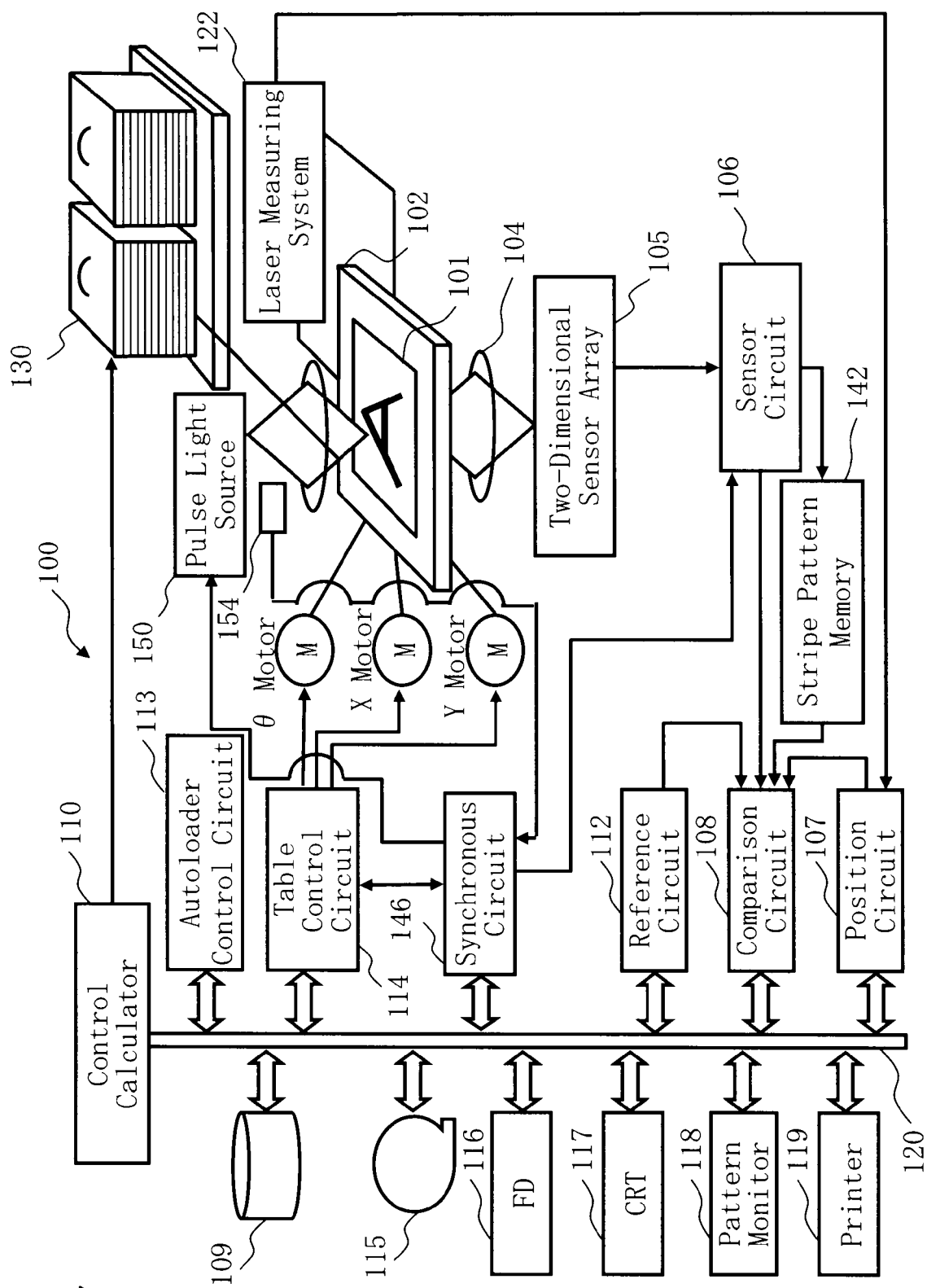
FIG. 17 shows a schematic diagram illustrating a structure of a pattern inspection apparatus described in Embodiment 3.
Figure 18:
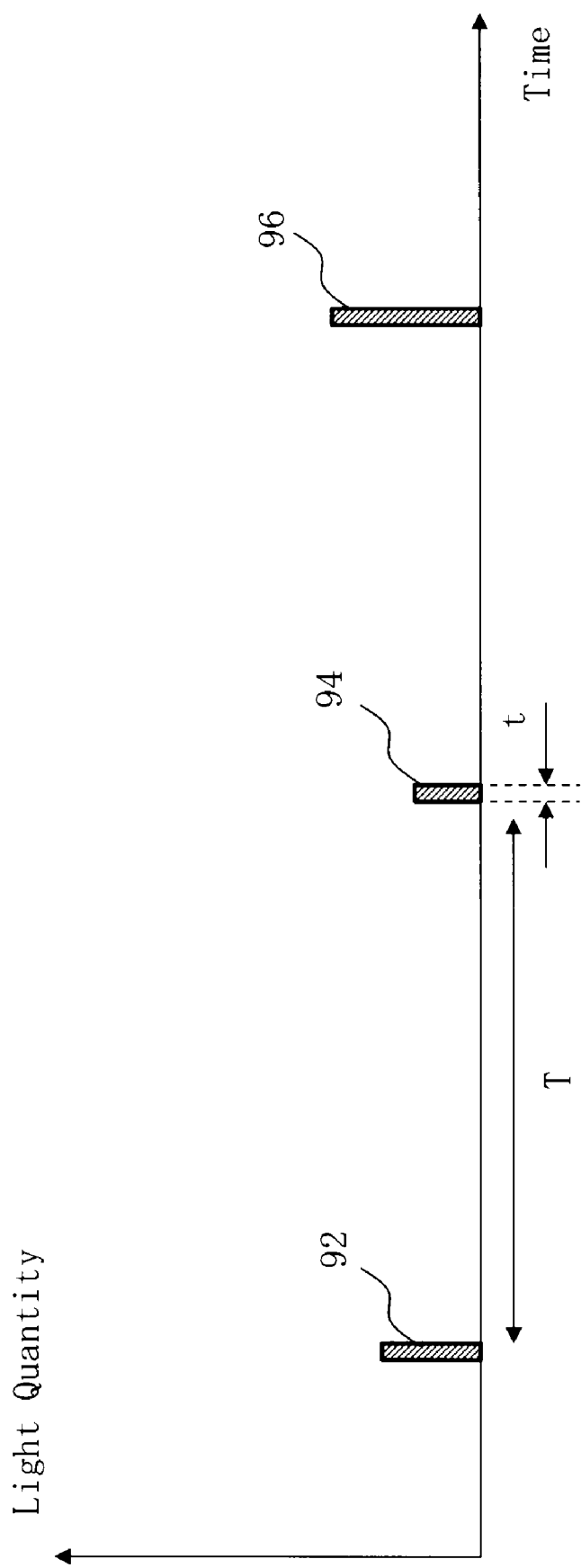
FIG. 18 shows an example of a photoperiod and a light quantity of a pulsed laser light source.

FIG. 17 shows a schematic diagram illustrating a structure of a pattern inspection apparatus described in Embodiment 3. In FIG. 17, structure elements are the same as those in FIG. 12 except for that a light quantity sensor 154 is added. FIG. 17 depicts structure elements necessary for describing Embodiment 3, and it should be understood that other structure elements generally necessary for the target workpiece inspection apparatus 100 may also be included therein. For the sake of simplicity, it is assumed that an aspheric lens is used in the optical system and there is neither aberration nor distortion.

In Embodiment 2, the XYθ table 102 (stage) is continuously moved at a fixed speed so that it may shift by a predetermined number of pixels (a number of natural number times one pixel) between pulses of a pulsed light. Moreover, each light receiving element 20 is irradiated with a plurality of times of pulsed lights, for example, 500 pulses. With respect to the change of the light quantity of each pulse, it is based on that the error can be reduced as total of the light quantity because of irradiation of a plurality of times of pulsed lights.

However, the change of the light quantity affects sensitivity of detecting a defect of translucency of the glass penetration part on a mask to be inspected, and sensitivity of a defect detection method of discerning a measurement error of a contact hole pattern based on the light quantity of a transmission light.

For this reason, in addition to the error reduction by irradiating with a plurality of pulses mentioned above, an error due to light quantity change, which still remains, will be corrected in Embodiment 3 as follows: The light quantity sensor 154 (light quantity measurement unit) measures a light quantity of a pulsed light emitted from the pulsed light source 150. The light quantity sensor 154 measures a light quantity of each pulse, and outputs the measurement result to the synchronous circuit 146. In the synchronous circuit 146, the sum total of the light quantities of a plurality of pulses irradiated on each pixel is calculated. For example, when each light receiving element 20 is irradiated with a plurality of times of pulsed lights, totally 1000 pulses, the sum total of light quantities of the pulsed lights for 1000 pulses emitted from the pulsed light source 150 is calculated. Then, the sum total of light quantities of the pulsed lights for the following 1000 pulses is calculated. Thus, the sum total of the light quantities of a predetermined number of pulses irradiated on each pixel is calculated, and change of the sum total light quantity is monitored. When the sum total light quantity of a pixel becomes smaller than that of the prior pixel as a result, the stage speed is made slow so that the number of times of irradiation of the pulsed light to be emitted on each pixel may be increased corresponding to the smallness, thereby making the sum total of the light quantity be close to a constant amount. Conversely, when the sum total light quantity of a pixel becomes larger than that of the prior pixel, the stage speed is made fast so that the number of times of irradiation of the pulsed light may be decreased corresponding to the largeness, thereby making the sum total of the light quantity be close to a constant amount. Since the XYθ table 102 continuously moves to be shifted by the number of pixels, a natural number times one pixel, between pulses, it is possible to correct errors due to light quantity change of the sum total light quantity of irradiation on each pixel, by making the value of the natural number variable. Then, during the continuous movement of the stage, the synchronous circuit 146 outputs a direction to change the natural number based on the sum total of light quantities to the table control circuit 114. The table control circuit 114 changes the stage speed while the stage is continuously moving, using the changed natural number. For example, when the number of light receiving elements in the moving direction is 4000 and the number of pixels which move between pulses is 4, a certain pixel is irradiated with a pulsed light of the number of pulses=4000/4=1000 times. Then, if the monitored sum total light quantity becomes large, the number of pixels is changed into 5 and the number of pulses with which the next pixel is irradiated is changed into 4000/5=800 times. In Embodiment 3, the more the number of pulses of pulsed light irradiation on the pixel becomes, the more effective the correction is.

While the embodiments have been described above with reference to specific examples, the present invention is not restricted to these specific ones. For example, although one light receiving element detects the surface of 100×100 nm on the target workpiece in the example above mentioned, it is also acceptable to detect 50×50 nm. Although the oscillation frequency of a pulsed laser is 40 kHz in the above description, a lower frequency, 10 kHz for example, may be used, and conversely a high frequency, 100 kHz for example, may also be used.

While description of the apparatus structure, control method, etc. not directly required for explaining the present invention is omitted, it is possible to suitably select and use some or all of them when needed. For example, although the structure of the control unit for controlling the inspection apparatus 100 is not described, it should be understood that a necessary control unit structure may be selected and used appropriately.

In addition, any other pattern inspection apparatus and pattern inspection method that include elements of the present invention and that can be appropriately modified by those skilled in the art are included within the scope of the present invention.

Additional advantages and modification will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A pattern inspection apparatus comprising:
a light source configured to emit a pulsed light;
a stage on which an inspection target workpiece is placed;
a sensor, including a plurality of light receiving elements two-dimensionally arrayed, configured to capture a pattern image in a two-dimensional region of the inspection target workpiece which is irradiated with the pulsed light, by using the plurality of light receiving elements;
a comparing unit configured to compare data of the pattern image with predetermined reference pattern image data;
wherein the stage moves to be shifted by a number of pixels, being the number of natural number times one pixel, between pulses of the pulsed light; and
further comprising a light quantity measurement unit configured to measure a light quantity of the pulsed light, wherein the natural number is changed based on the light quantity while the stage is continuously moving.

2. The apparatus according to claim 1, wherein the stage moves continuously.

3. The apparatus according to claim 1, wherein the sensor finishes outputting light quantity information for pixels in a two-dimensional region corresponding to the number of pixels of the pattern image captured, within a time period of the pulsed light.

4. The apparatus according to claim 1, further comprising a synchronous circuit configured to transmit a signal directing to emit lights to the light source in accordance with a position of the stage.

5. The apparatus according to claim 1, further comprising a synchronous circuit configured to detect that the stage has moved by the number of pixels, and transmit a signal directing to emit lights to the light source.

6. The apparatus according to claim 1, further comprising a correction unit configured to correct distortion of data of the pattern image.

7. The apparatus according to claim 6, wherein when an amount of the distortion is larger than a predetermined number of pixels, the distortion of the data of the pattern image is corrected.

8. A pattern inspection method comprising:
emitting a pulsed light;
capturing a pattern image in a two-dimensional region of an inspection target workpiece which is irradiated with the pulsed light, by using a sensor including a plurality of light receiving elements two-dimensionally arrayed, while moving a stage, on which the inspection target workpiece is placed, to be shifted by a number of pixels, being the number of natural number times one pixel, between pulses of the pulsed light;
comparing data of the pattern image with predetermined reference pattern image data, and outputting a comparing result; and
measuring a light quantity of the pulsed light and changing the natural number based on the light quantity while the stage is continuously moving.

* * * * *